US011969596B2

(12) United States Patent
Carmena et al.

(10) Patent No.: US 11,969,596 B2
(45) Date of Patent: Apr. 30, 2024

(54) IMPLANTABLE CLOSED-LOOP NEUROMODULATION DEVICE, SYSTEMS, AND METHODS OF USE

(71) Applicant: IOTA BIOSCIENCES, INC., Alameda, CA (US)

(72) Inventors: Jose M. Carmena, Berkeley, CA (US); Michel M. Maharbiz, El Cerrito, CA (US); Ryan Neely, El Cerrito, CA (US)

(73) Assignee: IOTA BIOSCIENCES, INC., Alameda, CA (US)

( * ) Notice: Subject to any disclaimer, the term of this patent is extended or adjusted under 35 U.S.C. 154(b) by 0 days.

(21) Appl. No.: 17/272,217

(22) PCT Filed: Aug. 28, 2019

(86) PCT No.: PCT/US2019/048647
§ 371 (c)(1),
(2) Date: Feb. 26, 2021

(87) PCT Pub. No.: WO2020/047152
PCT Pub. Date: Mar. 5, 2020

(65) Prior Publication Data
US 2021/0308462 A1 Oct. 7, 2021

Related U.S. Application Data

(60) Provisional application No. 62/724,253, filed on Aug. 29, 2018.

(51) Int. Cl.
*A61N 1/36* (2006.01)
*A61N 1/05* (2006.01)
*A61N 1/378* (2006.01)

(52) U.S. Cl.
CPC ....... *A61N 1/36135* (2013.01); *A61N 1/0556* (2013.01); *A61N 1/3787* (2013.01)

(58) Field of Classification Search
CPC .......................... A61N 1/0556; A61N 1/36135
See application file for complete search history.

(56) References Cited

U.S. PATENT DOCUMENTS 5,095,905 A 3/1992 Klepinski
5,282,468 A 2/1994 Klepinski
(Continued)

FOREIGN PATENT DOCUMENTS

CN 101048194 A 10/2007
CN 101939048 A 1/2011
(Continued)

OTHER PUBLICATIONS

Bertrand, A. et al. (Aug. 2014). "Beamforming Approaches for Untethered, Ultrasonic Neural Dust Motes for Cortical Recording: A Simulation Study," IEEE EMBC, pp. 2625-2628.
(Continued)

*Primary Examiner* — Alyssa M Alter
(74) *Attorney, Agent, or Firm* — MORRISON & FOERSTER LLP

(57) ABSTRACT

Described herein are implantable closed-loop neuromodulation devices, systems that includes such devices and an interrogator configured to emit ultrasonic waves that power the device, methods of using such devices and systems, and methods of modulating neural activity. The implantable device can include one or more curved members extending from a body. The curved members are configured to at least partially circumscribe a nerve, and include one or more electrode pads. The body includes an ultrasonic transducer configured to receive ultrasonic waves and convert energy from the ultrasonic waves into an electrical energy; and a computational circuit configured to receive a detection signal based on a detected electrophysiological signal, generate a stimulation signal based on the detection signal, and
(Continued)

operate the electrode pads of to emit an electrical pulse to the nerve based on the stimulation signal.

33 Claims, 4 Drawing Sheets

(56) References Cited

U.S. PATENT DOCUMENTS

| | | |
|---|---|---|
| 6,170,488 B1 | 1/2001 | Spillman, Jr. |
| 6,200,265 B1 | 3/2001 | Walsh |
| 6,885,888 B2 | 4/2005 | Rezai |
| 7,024,248 B2 | 4/2006 | Penner |
| 7,283,874 B2 | 10/2007 | Penner |
| 7,418,292 B2 | 8/2008 | Shafer |
| 7,616,990 B2 | 11/2009 | Chavan |
| 7,617,001 B2 | 11/2009 | Penner |
| 7,634,318 B2 | 12/2009 | Tran |
| 7,756,587 B2 | 7/2010 | Penner |
| 7,757,565 B2 | 7/2010 | Chakrabartty |
| 7,769,442 B2 | 8/2010 | Shafer |
| 7,778,704 B2 | 8/2010 | Rezai |
| 7,794,499 B2 | 9/2010 | Navarro |
| 7,894,907 B2 | 2/2011 | Cowan |
| 7,899,542 B2 | 3/2011 | Cowan |
| 8,285,389 B2 | 10/2012 | Libbus et al. |
| 8,340,778 B2 | 12/2012 | Tran |
| 8,412,338 B2 | 4/2013 | Faltys |
| 8,478,428 B2 | 7/2013 | Cowley |
| 8,494,642 B2 | 7/2013 | Cowan |
| 8,494,643 B2 | 7/2013 | Cowan |
| 8,515,520 B2 | 8/2013 | Brunnett et al. |
| 8,577,460 B2 | 11/2013 | Penner |
| 8,612,002 B2 | 12/2013 | Faltys |
| 8,660,648 B2 | 2/2014 | Chavan |
| 8,774,928 B2 | 7/2014 | Towe |
| 8,788,034 B2 | 7/2014 | Levine |
| 8,805,537 B1 | 8/2014 | Cong et al. |
| 8,849,412 B2 | 9/2014 | Perryman |
| 8,855,767 B2 | 10/2014 | Faltys |
| 8,874,233 B2 | 10/2014 | Mclaughlin |
| 8,886,339 B2 | 11/2014 | Faltys |
| 8,903,501 B2 | 12/2014 | Perryman |
| 8,934,972 B2 | 1/2015 | Penner |
| 8,996,116 B2 | 3/2015 | Faltys |
| 9,162,064 B2 | 10/2015 | Faltys |
| 9,174,041 B2 | 11/2015 | Faltys |
| 9,174,044 B2 | 11/2015 | Mclaughlin |
| 9,199,089 B2 | 12/2015 | Perryman |
| 9,211,409 B2 | 12/2015 | Tracey |
| 9,211,410 B2 | 12/2015 | Levine |
| 9,220,897 B2 | 12/2015 | Perryman |
| 9,242,103 B2 | 1/2016 | Perryman |
| 9,409,030 B2 | 8/2016 | Perryman |
| 9,544,068 B2 | 1/2017 | Arbabian |
| 9,566,449 B2 | 2/2017 | Perryman |
| 9,597,508 B2 | 3/2017 | Mclaughlin |
| 9,610,442 B2 | 4/2017 | Yoo et al. |
| 9,623,253 B2 | 4/2017 | Perryman |
| 9,662,490 B2 | 5/2017 | Tracey |
| 9,700,716 B2 | 7/2017 | Faltys |
| 9,717,921 B2 | 8/2017 | Perryman |
| 9,731,141 B2 | 8/2017 | Tran |
| 9,757,571 B2 | 9/2017 | Perryman |
| 9,789,314 B2 | 10/2017 | Perryman |
| 9,802,055 B2 | 10/2017 | Reinke |
| 9,833,621 B2 | 12/2017 | Levine |
| 9,849,286 B2 | 12/2017 | Levine |
| 9,925,384 B2 | 3/2018 | Perryman |
| 9,974,593 B2 | 5/2018 | Barman |
| 9,974,965 B2 | 5/2018 | Perryman |
| 9,993,651 B2 | 6/2018 | Faltys |
| 10,014,570 B2 | 7/2018 | Arbabian |
| 10,118,054 B2 | 11/2018 | Maharbiz |
| 10,177,606 B2 | 1/2019 | Charthad |
| 10,201,706 B2 | 2/2019 | Schwab |
| 10,220,203 B2 | 3/2019 | Faltys |
| 10,286,206 B2 | 5/2019 | Johnson et al. |
| 10,300,309 B2 | 5/2019 | Maharbiz |
| 10,300,310 B2 | 5/2019 | Maharbiz |
| 10,576,305 B2 | 3/2020 | Maharbiz |
| 10,682,530 B2 | 6/2020 | Maharbiz |
| 10,744,347 B2 | 8/2020 | Maharbiz |
| 10,765,865 B2 | 9/2020 | Maharbiz |
| 10,898,736 B2 | 1/2021 | Maharbiz et al. |
| 11,033,746 B2 | 6/2021 | Maharbiz et al. |
| 11,717,689 B2 | 8/2023 | Maharbiz et al. |
| 11,786,124 B2 | 10/2023 | Maharbiz et al. |
| 2003/0236557 A1 | 12/2003 | Whitehurst et al. |
| 2005/0010265 A1 | 1/2005 | Baru et al. |
| 2005/0075701 A1 | 4/2005 | Shafer |
| 2005/0075702 A1 | 4/2005 | Shafer |
| 2006/0136004 A1 | 6/2006 | Cowan |
| 2006/0178703 A1 | 8/2006 | Huston |
| 2006/0287678 A1 | 12/2006 | Shafer |
| 2007/0027486 A1 | 2/2007 | Armstrong |
| 2007/0093875 A1 | 4/2007 | Chavan |
| 2008/0108915 A1 | 5/2008 | Penner |
| 2009/0018403 A1 | 1/2009 | Black |
| 2009/0210042 A1 | 8/2009 | Kowalczewski |
| 2009/0248097 A1 | 10/2009 | Tracey |
| 2009/0275997 A1 | 11/2009 | Faltys |
| 2010/0145221 A1 | 6/2010 | Brunnett et al. |
| 2010/0268078 A1 | 10/2010 | Scarantino |
| 2010/0331933 A1 | 12/2010 | Carbunaru et al. |
| 2010/0331993 A1 | 12/2010 | Gradl |
| 2011/0054569 A1 | 3/2011 | Zitnik |
| 2012/0185007 A1 | 7/2012 | Ziegler et al. |
| 2013/0062527 A1 | 3/2013 | Hyde |
| 2013/0073000 A1 | 3/2013 | Chavan et al. |
| 2013/0165998 A1 | 6/2013 | Libbus et al. |
| 2013/0238044 A1 | 9/2013 | Penner |
| 2013/0310909 A1 | 11/2013 | Simon |
| 2013/0324891 A1 | 12/2013 | Towe |
| 2014/0094887 A1 | 4/2014 | True |
| 2014/0228905 A1 | 8/2014 | Bolea |
| 2014/0253435 A1 | 9/2014 | Boser |
| 2014/0336474 A1 | 11/2014 | Arbabian |
| 2014/0336727 A1 | 11/2014 | Perryman |
| 2015/0032178 A1 | 1/2015 | Simon et al. |
| 2015/0073510 A1 | 3/2015 | Perryman |
| 2015/0112233 A1 | 4/2015 | Towe |
| 2015/0241447 A1 | 8/2015 | Zitnik |
| 2015/0297900 A1 | 10/2015 | Perryman |
| 2016/0007893 A1 | 1/2016 | Roberts |
| 2016/0015988 A1 | 1/2016 | Perryman et al. |
| 2016/0023003 A1 | 1/2016 | Perryman |
| 2016/0038741 A1 | 2/2016 | Perryman |
| 2016/0038769 A1 | 2/2016 | Sullivan |
| 2016/0045743 A1 | 2/2016 | Liu |
| 2016/0067497 A1 | 3/2016 | Levine |
| 2016/0096016 A1 | 4/2016 | Tracey et al. |
| 2016/0114165 A1 | 4/2016 | Levine |
| 2016/0235329 A1 | 8/2016 | Bernstein |
| 2016/0331952 A1 | 11/2016 | Faltys |
| 2016/0331962 A1 | 11/2016 | Schwab |
| 2016/0361535 A1 | 12/2016 | Perryman et al. |
| 2016/0367823 A1 | 12/2016 | Cowan et al. |
| 2017/0001003 A1 | 1/2017 | Pivonka |
| 2017/0007853 A1 | 1/2017 | Alford |
| 2017/0095198 A1 | 4/2017 | Towe |
| 2017/0095667 A1 | 4/2017 | Yakovlev |
| 2017/0100588 A1 | 4/2017 | Schwab |
| 2017/0100589 A1 | 4/2017 | Schwab |
| 2017/0100604 A1 | 4/2017 | Schwab |
| 2017/0100605 A1 | 4/2017 | Schwab |
| 2017/0117753 A1 | 4/2017 | Charthad |
| 2017/0125892 A1 | 5/2017 | Arbabian |
| 2017/0173328 A1 | 6/2017 | Ostroff |
| 2017/0197082 A1 | 7/2017 | Pang |
| 2017/0202467 A1 | 7/2017 | Zitnik et al. |
| 2017/0266454 A1 | 9/2017 | Amir et al. |
| 2017/0281954 A1 | 10/2017 | Reinke et al. |
| 2017/0304630 A1 | 10/2017 | Plachta |
| 2017/0319858 A1 | 11/2017 | Radziemski et al. |

(56) References Cited

U.S. PATENT DOCUMENTS

| | | |
|---|---|---|
| 2018/0008828 A1 | 1/2018 | Perryman |
| 2018/0021214 A1 | 1/2018 | Tracey |
| 2018/0021580 A1 | 1/2018 | Tracey |
| 2018/0027077 A1 | 1/2018 | Melodia |
| 2018/0055393 A1 | 3/2018 | Cantwell |
| 2018/0085593 A1 | 3/2018 | Fayram et al. |
| 2018/0085605 A1 | 3/2018 | Maharbiz |
| 2018/0117319 A1 | 5/2018 | Chew |
| 2018/0117320 A1 | 5/2018 | Levine |
| 2018/0133474 A1 | 5/2018 | Meadows et al. |
| 2018/0154142 A1 | 6/2018 | Guo et al. |
| 2018/0154156 A1 | 6/2018 | Clark et al. |
| 2018/0161002 A1 | 6/2018 | Alford et al. |
| 2018/0169423 A1 | 6/2018 | Perryman |
| 2018/0236248 A1 | 8/2018 | Perryman |
| 2018/0264277 A1 | 9/2018 | Perryman |
| 2018/0289970 A1 | 10/2018 | Faltys |
| 2018/0289971 A1 | 10/2018 | Yeh et al. |
| 2019/0022384 A1 | 1/2019 | Kai et al. |
| 2019/0022427 A1 | 1/2019 | Maharbiz |
| 2019/0022428 A1 | 1/2019 | Maharbiz |
| 2019/0150881 A1 | 5/2019 | Maharbiz |
| 2019/0150882 A1 | 5/2019 | Maharbiz |
| 2019/0150883 A1 | 5/2019 | Maharbiz |
| 2019/0150884 A1 | 5/2019 | Maharbiz |
| 2019/0290913 A1 | 9/2019 | Blancou et al. |
| 2019/0321640 A1 * | 10/2019 | Carmena ............ H02J 50/15 |
| 2019/0321644 A1 | 10/2019 | Maharbiz |
| 2020/0023208 A1 | 1/2020 | Maharbiz |
| 2020/0023209 A1 | 1/2020 | Maharbiz |
| 2020/0114175 A1 | 4/2020 | Maharbiz |
| 2020/0230441 A1 | 7/2020 | Maharbiz |
| 2020/0257136 A1 | 8/2020 | Arbabian et al. |
| 2020/0289857 A1 | 9/2020 | Maharbiz |
| 2020/0324148 A1 | 10/2020 | Maharbiz |
| 2020/0391035 A1 | 12/2020 | Donega et al. |
| 2021/0268294 A1 | 9/2021 | Maharbiz et al. |
| 2022/0047869 A1 | 2/2022 | Carmena et al. |
| 2022/0062650 A1 | 3/2022 | Maharbiz et al. |
| 2022/0143414 A1 | 5/2022 | Maharbiz et al. |
| 2022/0296886 A1 | 9/2022 | Bashirullah et al. |
| 2023/0089015 A1 | 3/2023 | Maharbiz et al. |
| 2023/0095948 A1 | 3/2023 | Maharbiz et al. |
| 2023/0233851 A1 | 7/2023 | Neely et al. |
| 2023/0301514 A1 | 9/2023 | Lepe et al. |

FOREIGN PATENT DOCUMENTS

| | | |
|---|---|---|
| CN | 102821814 A | 12/2012 |
| CN | 104254291 A | 12/2014 |
| CN | 104623808 A | 5/2015 |
| CN | 104736197 A | 6/2015 |
| CN | 105228513 A | 1/2016 |
| CN | 105848710 A | 8/2016 |
| CN | 107073257 A | 8/2017 |
| CN | 107106840 A | 8/2017 |
| CN | 107614057 A | 1/2018 |
| CN | 107789730 A | 3/2018 |
| CN | 107864633 A | 3/2018 |
| EP | 1745818 A1 | 1/2007 |
| EP | 2515996 A2 | 10/2012 |
| EP | 2355893 B1 | 12/2013 |
| EP | 2667942 A2 | 12/2013 |
| EP | 2694154 A1 | 2/2014 |
| EP | 2741810 A1 | 6/2014 |
| EP | 2162185 B1 | 7/2015 |
| EP | 1648559 B1 | 9/2015 |
| EP | 2928557 A2 | 10/2015 |
| EP | 2707094 B1 | 2/2016 |
| EP | 2337609 B1 | 8/2016 |
| EP | 2755718 B1 | 12/2017 |
| EP | 3259015 | 12/2017 |
| EP | 3259017 | 12/2017 |
| EP | 2736592 B1 | 1/2018 |
| EP | 3285856 | 2/2018 |
| EP | 2651431 B1 | 3/2018 |
| EP | 3294376 | 3/2018 |
| EP | 3338855 A1 | 6/2018 |
| EP | 2440284 B1 | 9/2018 |
| EP | 3403690 A1 | 11/2018 |
| EP | 3057652 B1 | 7/2023 |
| JP | 2007021225 A | 2/2007 |
| JP | 2011513038 A | 4/2011 |
| JP | 2014525288 A | 9/2014 |
| WO | 2005032653 A1 | 4/2005 |
| WO | 2006029257 A2 | 3/2006 |
| WO | 2006138068 A2 | 12/2006 |
| WO | 2007050657 A1 | 5/2007 |
| WO | 2007090159 A1 | 8/2007 |
| WO | 2009114689 A1 | 9/2009 |
| WO | 2009146030 A1 | 12/2009 |
| WO | 2010059617 A2 | 5/2010 |
| WO | 2010059617 A3 | 9/2010 |
| WO | 2010144578 A2 | 12/2010 |
| WO | 2010144578 A3 | 3/2011 |
| WO | 2011028763 A2 | 3/2011 |
| WO | 2011079309 A2 | 6/2011 |
| WO | 2011028763 A3 | 7/2011 |
| WO | 2011079309 A3 | 11/2011 |
| WO | 2012057868 A1 | 5/2012 |
| WO | 2012083259 A2 | 6/2012 |
| WO | 2012103519 A2 | 8/2012 |
| WO | 2012138782 A1 | 10/2012 |
| WO | 2012154865 A2 | 11/2012 |
| WO | 2012154865 A3 | 1/2013 |
| WO | 2013019757 A2 | 2/2013 |
| WO | 2013025632 A1 | 2/2013 |
| WO | 2013028428 A1 | 2/2013 |
| WO | 2013040549 A1 | 3/2013 |
| WO | 2013044207 A1 | 3/2013 |
| WO | 2012083259 A3 | 9/2013 |
| WO | 2013134479 A1 | 9/2013 |
| WO | 2012103519 A3 | 3/2014 |
| WO | 2013019757 A3 | 5/2014 |
| WO | 2014089299 A2 | 6/2014 |
| WO | 2014153218 A1 | 9/2014 |
| WO | 2014153219 A1 | 9/2014 |
| WO | 2014153223 A1 | 9/2014 |
| WO | 2014153228 A1 | 9/2014 |
| WO | 2014089299 A3 | 10/2014 |
| WO | 2014169145 A1 | 10/2014 |
| WO | 2015127476 A1 | 8/2015 |
| WO | 2015142842 A2 | 9/2015 |
| WO | 2015142842 A3 | 11/2015 |
| WO | 2016028608 A1 | 2/2016 |
| WO | 2016112398 A1 | 7/2016 |
| WO | 2016134197 A1 | 8/2016 |
| WO | 2016134199 A1 | 8/2016 |
| WO | 2016168798 A1 | 10/2016 |
| WO | 2016170510 A1 | 10/2016 |
| WO | 2016183353 A1 | 11/2016 |
| WO | 2016187114 A1 | 11/2016 |
| WO | 2017087681 A1 | 5/2017 |
| WO | WO-2017087681 A1 * | 5/2017 ........... A61N 1/0551 |
| WO | 2017143185 A1 | 8/2017 |
| WO | 2017143191 A1 | 8/2017 |
| WO | 2018005848 A1 | 1/2018 |
| WO | 2018009905 A2 | 1/2018 |
| WO | 2018009908 A1 | 1/2018 |
| WO | 2018009910 A1 | 1/2018 |
| WO | 2018009911 A1 | 1/2018 |
| WO | 2018009912 A1 | 1/2018 |
| WO | 2018017591 A1 | 1/2018 |
| WO | 2018009905 A3 | 2/2018 |
| WO | 2018081763 A1 | 5/2018 |
| WO | 2018081826 A1 | 5/2018 |
| WO | 2018087193 A1 | 5/2018 |
| WO | 2018089895 A2 | 5/2018 |
| WO | 2018089895 A3 | 6/2018 |
| WO | 2018118857 A1 | 6/2018 |
| WO | 2018118860 A1 | 6/2018 |
| WO | 2018118861 A1 | 6/2018 |
| WO | 2018118864 A1 | 6/2018 |
| WO | 2018118866 A1 | 6/2018 |

(56) References Cited

FOREIGN PATENT DOCUMENTS

| | | |
|---|---|---|
| WO | 2019075203 A1 | 4/2019 |
| WO | 2019122903 A2 | 6/2019 |
| WO | 2019122908 A1 | 6/2019 |
| WO | 2019122903 A3 | 8/2019 |
| WO | 2019204769 A1 | 10/2019 |
| WO | 2019204773 A1 | 10/2019 |
| WO | 2020117967 A1 | 6/2020 |
| WO | 2020142732 A1 | 7/2020 |
| WO | 2020142733 A1 | 7/2020 |
| WO | 2020254798 A1 | 12/2020 |
| WO | 2021077020 A1 | 4/2021 |
| WO | 2021077022 A1 | 4/2021 |
| WO | 2021105699 A1 | 6/2021 |
| WO | 2021105708 A1 | 6/2021 |
| WO | 2021108810 A1 | 6/2021 |
| WO | 2021168163 A1 | 8/2021 |
| WO | 2021168229 A1 | 8/2021 |
| WO | 2021248013 A1 | 12/2021 |
| WO | 2022035889 A1 | 2/2022 |
| WO | 2022046770 A1 | 3/2022 |
| WO | 2023183891 A2 | 9/2023 |

OTHER PUBLICATIONS

Beyer, G.P. et al. (Jan. 1, 2008). "An Implantable MOSFET Dosimeter for the Measurement of Radiation Dose in Tissue During Cancer Therapy," IEEE Sensors Journal 8(1):38-51.

Celinskis, D. et al. (Aug. 26, 2014). "Wireless Impedance Measurements for Monitoring Peripheral Vascular Disease," 36th Annual International Conference of the IEEE Engineering in Medicine and Biology Society pp. 6937-6940.

Grossman, N. et al. (Jun. 1, 2017). "Noninvasive Deep Brain Stimulation via Temporally Interfering Electric Fields," Cell 169:1029-1041.

International Preliminary Report on Patentability, dated Mar. 2, 2021 for PCT Application No. PCT/US2019/048647, filed Aug. 28, 2019, 7 pages.

International Preliminary Report on Patentability, dated Oct. 20, 2020 for PCT Application No. PCT/US2019/028385, filed Apr. 19, 2019, 7 pages.

International Search Report and Written Opinion, dated Aug. 29, 2019 for PCT Application No. PCT/US2019/028385, filed Apr. 19, 2019, 10 pages.

International Search Report and Written Opinion, dated Nov. 21, 2019, for PCT Application No. PCT/US2019/048647, filed Aug. 28, 2019, 9 pages.

Kay, J. (May 4, 2017). "Rodent Wearable Ultrasound Interrogation System for Wireless Neural Recording", Berkeley EECS, Technical Report No. UCS/EECS-2017-27, 50 pages.

Mazzilli, F. et al. (Aug. 31-Sep. 4, 2010). "In-Vitro Platform to Study Ultrasound as Source for Wireless Energy Transfer and Communication for Implanted Medical Devices," 32nd Annual International Conference of the IEEE EMBS, pp. 3751-3754.

Peisino, M. (May 17, 2013). "Deeply Implanted Medical Device Based on a Novel Ultrasonic Telemetry Technology," École Polytechnique Fédérale De Lausanne pp. 148.

Piech, D.K. et al. (2017). "Rodent Wearable Ultrasound System for Wireless Neural Recording," 39th Annual International Conference of the IEEE Engineering in Medicine and Biology Society, EMBC, 5 pages.

Seo, D. (May 1, 2016). "Design of Ultrasonic Power Link for Neural Dust", Technical Report No. UCB/EECS-2016-21, Electrical Engineering and Computer Sciences University of California at Berkeley, 71 pages.

Seo, D. et al. (2015). "Ultrasonic Beamforming System for Interrogating Multiple Implantable Sensors," IEEE, pp. 2673-2676.

Seo, D. et al. (Apr. 1, 2015, e-pub. Aug. 7, 2014). "Model Validation of Untethered, Ultrasonic Neural Dust Motes for Cortical Recording," J. of Neuroscience Methods 244:114-122.

Seo, D. et al. (Aug. 3, 2016). "Wireless Recording in the Peripheral Nervous System with Ultrasonic Neural Dust," Neuron 91:529-539.

Seo, D. et al. (Jul. 8, 2013). "Neural Dust: Ultrasonic Low Power Solution for Chronic Brain-Machine Interfaces," Dept. of Electrical Engineering and Computer Sciences Berkley, CA. pp.1-11.

Tang, H.-Y. et al. (Dec. 2015). "Miniaturizing Ultrasonic System for Portable Health Care and Fitness," IEEE Transactions on Biomedical Circuits and Systems 9(6):767-776.

Taylor, J. et al. (2004). "Multiple-Electrode Nerve Cuffs for Low-Velocity and Velocity-Selective Neural Recording," Medical & Biological Engineering & Computing 42:634-643.

Tsai, J.-Y. et al. (2011). "Ultrasonic Wireless Power and Data Communication for Neural Stimulation," 2011 IEEEE International Ultrasonics Symposium pp. 1052-1055.

Weissleder, R. et al. (May 1, 2001). "Molecular Imaging," Radiology, Radiological Society of North America, Inc. 219(2):316-333.

Wodlinger, B. et al. (Oct. 2009). "Localization and Recovery of Peripheral Neural Sources With Beamforming Algorithms," IEEE Transactions on Neural Systems and Rehabilitation Engineering 17(5):461-468, 18 pages.

Arbabian, A. et al. (Dec. 1, 2016). "Sound Technologies, Sound Bodies: Medical Implants With Ultrasonic Links," IEEE Microwave Magazine 17(12):39-54.

Extended European Search Report, dated Apr. 8, 2022, for European Patent Application 19854384.5, 8 pages.

Extended European Search Report, dated Jan. 19, 2022, for European Patent Application 19788423.2, 12 pages.

Mazzilli, F. et al. (Oct. 2014). "A 10.5 cm Ultrasound Link for Deep Implanted Medical Devices," IEEE Transactions on Biomedical Circuits and Systems 8(5):738-750.

Brown, G.L. et al. (1957). "The Output of Sympathetic Transmitter From the Spleen of the Cat," J. Physiol. 138:81-102.

Carnevale, D. et al. (Sep. 27, 2016). "A Cholinergic-Sympathetic Pathway Primes Immunity In Hypertension and Mediates Brain-To-Spleen Communication," Nature Communications, 7:13035, 13 pages.

Coldewey, D. (Dec. 27, 2018). "Iota Biosciences Raises $15M to Produce In-Body Sensors Smaller Than a Grain of Rice," TechCrunch, 4 pages.

Eckberg, D.L. et al. (1988). "Baroreflex Modulation of Sympathetic Activity and Sympathetic Neurotransmitters in Humans," Acta Physiol. Scand. 133:221-231.

Guyot, M. et al. (2019, e-pub. Mar. 15, 2019). "Apical Splenic Nerve Electrical Stimulation Discloses an Anti-Inflammatory Pathway Relying on Adrenergic and Nicotinic Receptors in Myeloid Cells," Brain, Behavior, and Immunity 80:238-246.

Hellyer, J. et al. (Feb. 2014). "Autonomic Nerve Activity and Blood Pressure in Ambulatory Dogs," Heart Rhythm, 11(2):307-313, 14 pages.

International Preliminary Report on Patentability, dated Apr. 19, 2022, for PCT Application No. PCT/US2020/056159, filed Oct. 16, 2020, 10 pages.

International Preliminary Report on Patentability, dated Apr. 19, 2022, for PCT Application No. PCT/US2020/056161, filed Oct. 16, 2020, 8 pages.

International Search Report and Written Opinion, dated Feb. 26, 2021, for PCT Application No. PCT/US2020/056161, filed Oct. 16, 2020, 13 pages.

International Search Report and Written Opinion, ated Jan. 21, 2021 for PCT Application No. PCT/US2020/056159, filed Oct. 16, 2020, 13 pages.

Katafuchi, T. et al. (1993). "Roles of Sympathetic Nervous System in the Suppression of Cytotoxicity of Splenic Natural Killer Cells in the Rat," J. of Physiology 465:343-357.

Kees, M.G. et al. (2003). "Via β-Adrenoceptors, Stimulation of Extrasplenic Sympathetic Nerve Fibers Inhibits Lipopolysaccharide-Induced TNF Secretion in Perfused Rat Spleen," J. of Neuroimmunology 145:77-85.

Kirpekar, S.M. et al. (1967). "Release of Noradrenaline by Splenic Nerve Stimulation and Its Dependence of Calcium," J. Physiol. 188:219-234.

(56) References Cited

OTHER PUBLICATIONS

Niijima, A. et al. (1991). "The Effects of Interleukin-1β on the Activity of Adrenal, Splenic and Renal Sympathetic Nerves in the Rat," J. of the Autonomic Nervous System 36:183-192.

Ninomiya, I. et al. (Nov. 1971). "Sympathetic Nerve Activity to the Spleen, Kidney, and Heart in Response to Baroceptor Input," American J. of Physiology 221(5):1346-1351.

Perrotta, M. et al. (2018, e-pub. Feb. 24, 2018). "The Interactions of the Immune System and the Brain in Hypertension," Current Hypertension Reports 20:7, 6 pages.

Rayburn, E.R. et al. (2009). "Anti-Inflammatory Agents for Cancer Therapy," Mol. Cell. Pharmacol. 1(1):29-43, 20 pages.

Robertson, M.J. (Feb. 1, 2002). "Role of Chemokines in the Biology of Natural Killer Cells," J. Leukoc. Biol. 71:173-183.

Rosenberg, J. et al. (Mar. 2018, e-pub. Dec. 14. 2017). "CD+ T Cells and NK Cells: Parallel and Complementary Soldiers of Immunotherapy," Curr. Opin. Chem. Eng. 19:1-22.

Simon, T. et al. (Nov. 11, 2019). "Stimulation of Splenic Neurovascular Bundle Protect Mice from Developing Collagen-Induced Arthritis," Abstract No. 998, 2 pages.

Straub, R. H. et al. (Jul. 2000). "A Bacteria-Induced Switch of Sympathetic Effector Mechanisms Augments Local Inhibition of TNF-α and IL-6 Secretion in the Spleen," The FASEB Journal 14:1380-1388.

Straub, R.H. et al. (2002). "Immunoregulation of IL-6 Secretion by Endogenous and Exogenous Adenosine and by Exogenous Purinergic Agonists in Splenic Tissue Slices," J. of Neuroimmunology 125:73-81.

U.S. Appl. No. 17/767,409, Carmena et al., filed Apr. 7, 2022.
U.S. Appl. No. 18/343,707, Maharbiz et al., filed Jun. 28, 2023.
Williams, J.M. et al. (1981). "Sympathetic Innervation of Murine Thymus and Spleen: Evidence for a Functional Link Between the Nervous and Immune Systems," Brain Research Bulletin 6:83-94.
U.S. Appl. No. 17/767,419, Maharbiz et al., filed Oct. 16, 2020.
U.S. Appl. No. 18/244,174, Maharbiz et al., filed Sep. 8, 2023.
U.S. Appl. No. 18/475,136, Carmena et al., filed Sep. 26, 2023. (Copy not submitted herewith pursuant to the waiver of 37 C.F.R. § 1.98(a)(2)(iii) issued by the Office on Sep. 21, 2004).

* cited by examiner

IMPLANTABLE CLOSED-LOOP NEUROMODULATION DEVICE, SYSTEMS, AND METHODS OF USE

CROSS-REFERENCE TO RELATED APPLICATION

This application is a U.S. national phase application under 35 U.S.C. § 371 of International Application No. PCT/US2019/048647, filed on Aug. 28, 2019, which claims the priority benefit of U.S. Provisional Application No. 62/724,253, filed on Aug. 29, 2018, the entire disclosure of each of which is incorporated herein by reference for all purposes.

TECHNICAL FIELD

The present invention relates to an implantable closed-loop neuromodulation device, and methods of using the implantable device.

BACKGROUND

The peripheral nervous system of an individual operates activity of vital organs and physiological homeostasis with tight control. Electrical pulses transmitted through nerves can alter, for example, heart rates, inflammation, and bladder or bowel control. Certain medical conditions can arise when these neural signals fail to properly control the body, either by over-stimulating or under-stimulating target organs.

Invasive methods have been developed for treating abnormal physiological activity by controlling the electrical signals of the peripheral nervous system. Such methods can include implanting electrodes into the body of a patient, with the tips of the electrodes contacting target nerves. These electrodes generally have long leads that attach to an external device or a bulky implanted device, which subject the patient to substantial risk of infection or displacement of the electrodes. Additionally, because many of the methods are so invasive, certain treatments are limited to clinical settings, and cannot be used as an at-home remedy. Wholly implantable devices have been developed for less invasive treatment, but such devices are too large to be placed in many locations of the body. Therefore, the implanted devices require the use of long leads, which can be displaced or break.

Closed-loop neuromodulation devices can emit a neuromodulating electrical pulse in response to receiving a signal, such as an action potential transmitted by a nerve. However, signals transmitted by nerves can be compounded (i.e., compound action potentials), and can transmitted by one of several fascicles located within a nerve bundle. Therefore, many closed-loop devices detecting signals from a nerve are not sufficiently precise to distinguish between benign action potentials and action potentials originating form targeted downstream nerves. Additionally, neural stimulation of many neuromodulation devices emit a broad electrical pulse to a nerve, which results in stimulation of off-target downstream nerves. There continues to be a need for implantable closed-loop devices that can stimulate specific nerves in a controlled manner and with limited risks and side effects.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE INVENTION

Described herein are implantable closed-loop neuromodulation device and methods of using the implantable device.

For example, in one embodiment an implantable closed-loop neuromodulation device, comprises: one or more curved members extending from a body, the curved members configured to at least partially circumscribe a nerve, wherein the curved members comprise one or more electrode pads; the body comprising: an ultrasonic transducer configured to receive ultrasonic waves and convert energy from the ultrasonic waves into an electrical energy; and a computational circuit electrically connected to the one or more electrode pads, configured to: receive a detection signal based on a detected electrophysiological signal, generate a stimulation signal based on the detection signal, and operate the one or more electrode pads of the one or more curved members to emit an electrical pulse to the nerve based on the stimulation signal.

In some embodiments, the one or more curved members comprises a plurality of electrode pads positioned along the curved member.

In some embodiments, the one or more curved members comprises a curved electrode pad that at least partially circumscribes the nerve. In some embodiments, at least one of the one or more curved members comprises two or more curved electrode pads that each at least partially circumscribes the nerve on the same curved member.

In some embodiments, the one or more electrode pads or the plurality of electrode pads comprises three or more electrode pads.

In some embodiments, an implantable closed-loop neuromodulation device comprises one or more curved members extending from a body, each curved member comprising a plurality of electrode pads configured to be radially positioned around an axis parallel to the length of a nerve; the body comprising: an ultrasonic transducer configured to receive ultrasonic waves and convert energy from the ultrasonic waves into an electrical energy; and a computational circuit electrically connected to the plurality of electrode pads, configured to: receive a detection signal based on a detected electrophysiological signal, generate a stimulation signal based on the detection signal, and operate the plurality of electrode pads of at least one of the one or more curved members to emit an electrical pulse to the nerve based on the stimulation signal.

In some embodiments, the plurality of electrode pads comprises three or more electrode pads. In some embodiments, the electrode pads within the plurality of electrode pads are radially positioned in a common plane of the nerve. In some embodiments, the device is configured to detect the electrophysiological signal from a targeted subset of nerve fibers within the nerve. In some embodiments, the device is configured to detect the electrophysiological signal from one or more targeted fascicles within the nerve, one or more targeted afferent nerve fibers within the nerve, or one or more targeted efferent nerve fibers within the nerve. In some embodiments, the device is configured to detect the electrophysiological signal from two or more different targeted fascicles within the nerve. In some embodiments, the device is configured to emit the electrical pulse to a targeted subset of nerve fibers within the nerve. In some embodiments, the device is configured to emit the electrical pulse to one or more targeted fascicles within the nerve, one or more targeted afferent nerve fibers within the nerve, or one or more targeted efferent nerve fibers within the nerve. In some embodiments, the device is configured to emit the electrical pulse to two or more different targeted fascicles within the nerve.

In some embodiments, the device is configured to detect the electrophysiological signal from a first targeted subset of nerve fibers within the nerve, and to emit the electrical pulse to a second targeted subset of nerve fibers within the nerve, wherein the first targeted subset of nerve fibers and the second targeted subset of nerve fibers are the same or different.

In some embodiments, the body further comprises a battery configured to receive the electrical energy from the ultrasonic transducer and power the computational circuit.

In some embodiments, the device comprises a non-transitory memory. In some embodiments, the non-transitory memory is configured to store data comprising data based on the detected electrophysiological signal, data based on the emitted electrical pulse, or data based on a detected or measured physiological condition. In some embodiments, the non-transitory memory is configured to store data received from an interrogator. In some embodiments, the ultrasonic transducer is configured to emit ultrasonic backscatter waves that encode at least a portion of the data. In some embodiments, the data comprises a time stamp, a velocity, a direction, an amplitude, a frequency, or a waveform of the detected electrophysiological signal or the emitted electrical pulse. In some embodiments, the non-transitory memory is configured to store data acquired over a period of time. In some embodiments, the non-transitory memory stores one or more template detection signals or one or more template pulses. In some embodiments, the computational circuit is configured to generate the stimulation signal by comparing the detection signal to the one or more template detection signals. In some embodiments, generating the stimulation signal comprises retrieving a template pulse from the non-transitory memory, and generating the stimulation signal based on the retrieved template pulse.

In some embodiments, the stimulation signal is generated using a mathematical relationship between the detection single and the stimulation signal.

In some embodiments, the device further comprises a sensor configured to detect or measure a physiological condition. In some embodiments, the physiological condition is temperature, pH, pressure, heart rate, strain, or presence or amount of an analyte. In some embodiments, the detection signal comprises a detected electrophysiological pulse component and an additional detected physiological condition component.

In some embodiments, the device comprises a first curved member comprising a first set of one or more electrode pads and a second curved member comprising a second set of one or more electrode pads, wherein the first curved member and the second curved member are each configured at least partially circumscribe the nerve at different positions along the length of the nerve. In some embodiments, the first set of one or more electrode pads comprises a plurality of electrode pads positioned along the first curved member, the second set of one or more electrode pads comprises a plurality of electrode pads positioned along the second curved member, or both. In some embodiments, the first set of one or more electrode pads comprises a curved electrode pad that at least partially circumscribes the nerve, the second set of one or more electrode pads comprises a curved electrode pad that at least partially circumscribes the nerve, or both. In some embodiments, the first set of electrode pads and the second set of electrode pads are configured to detect the electrophysiological signal transmitted by the nerve. In some embodiments, the device further comprises a third curved member comprising a third plurality of electrode pads, wherein the third curved member is configured to be at least partially circumscribe the nerve at a position between the first curved member and the second curved member along the length of the nerve. In some embodiments, the third set of electrode pads comprises a plurality of electrode pads positioned along the third curved member. In some embodiments, the third set of electrode pads comprises a curved electrode pad that at least partially circumscribes the nerve. In some embodiments, the computational circuit is configured to determine a subset of nerve fibers that transmits the electrophysiological signal based on the electrophysiological signal detected by one or more of the first plurality of electrode pads, the second plurality of electrode pads, or the third plurality of electrode pads. In some embodiments, the subset of nerve fibers that transmits the electrophysiological signal is further determined based on data received from an interrogator. In some embodiments, the first plurality of electrode pads, the second plurality of electrode pads, or the third plurality of electrode pads are configured to emit the electrical pulse to the nerve. In some embodiments, the electrode pads within the first plurality of electrode pads, the second plurality of electrode pads, or the third plurality of electrode pads are configured to be selectively activated to emit the electrical pulse to a targeted subset of nerve fibers within the nerve.

In some embodiments, the device comprises: a first curved member comprising a first plurality of electrode pads, and a second curved member comprising a second plurality of electrode pads, the first plurality of electrode pads and the second plurality of electrode pads configured to detect the electrophysiological signal transmitted by the nerve; and a third curved member comprising a third plurality of electrode pads, and a fourth curved member comprising a fourth plurality of electrode pads, the third plurality of electrode pads and the fourth plurality of electrode pads configured to emit the electrical pulse; wherein the first plurality of electrodes, the second plurality of electrodes, the third plurality of electrodes, and the fourth plurality of electrodes are each configured to be radially positioned around the axis parallel to the nerve at different positions along the length of the nerve. In some embodiments, the third curved member and the fourth curved member are positioned between the first curved member and the second curved member along the length of the nerve. In some embodiments, the device further comprises a fifth curved member comprising a fifth plurality of electrode pads configured to detect the electrophysiological signal. In some embodiments, the fifth curved member is positioned between the third curved member and the fourth curved member along the length of the nerve. In some embodiments, the computational circuit is configured to determine a subset of nerve fibers that transmits the electrophysiological signal based on the electrophysiological signal detected by one or more of the first plurality of electrode pads, the second plurality of electrode pads, or the fifth plurality of electrode pads. In some embodiments, the subset of nerve fibers that transmits the electrophysiological signal is further determined based on data received from an interrogator. In some embodiments, the electrode pads within the third plurality of electrode pads or the fourth plurality of electrode pads are configured to be selectively activated to emit the electrical pulse to a targeted subset of nerve fibers within the nerve.

In some embodiments, the device comprises a first curved member comprising a first electrode pad and a second curved member, wherein the first of electrode pad and the second electrode pad are each configured to at least partially surround the axis parallel to the length of the nerve at different positions along the length of the nerve. In some embodiments, the first electrode pad and the second electrode pad are configured to detect the electrophysiological signal transmitted by the nerve. In some embodiments, the device further comprises a third curved member comprising a third electrode pad configured to at least partially surround the axis parallel to the length of the nerve at a position between the first curved member and the second curved member along the length of the nerve. In some embodiments, the computational circuit is configured to determine a subset of nerve fibers that transmits the electrophysiological signal based on the electrophysiological signal detected by one or more of the first electrode pad, the second electrode pad, or the third electrode pad. In some embodiments, the subset of nerve fibers that transmits the electrophysiological signal is further determined based on data received from an interrogator. In some embodiments, the first electrode pad, the second electrode pad, or the third electrode pad is configured to emit the electrical pulse to the nerve. In some embodiments, the first electrode pad, the second electrode pad, or the third electrode pad is configured to be selectively activated to emit the electrical pulse to a targeted subset of nerve fibers within the nerve.

In some embodiments, the device comprises: a first curved member comprising a first of electrode pad and a second curved member comprising a second electrode pad, the first electrode pad and the second electrode pad configured to detect the electrophysiological signal transmitted by the nerve; and a third curved member comprising a third electrode pad, and a fourth curved member comprising a fourth electrode pad, the third electrode pas and the fourth electrode pad configured to emit the electrical pulse; wherein the first electrode pad, the second electrode pad, the third electrode pad, and the fourth electrode pad are configured to at least partially surround an axis parallel to the length of a nerve at different positions along the length of the nerve. In some embodiments, the third curved member and the fourth curved member are positioned between the first curved member and the second curved member along the length of the nerve. In some embodiments, the device further comprises a fifth curved member comprising a fifth electrode pad configured to detect the electrophysiological signal. In some embodiments, the fifth curved member is positioned between the third curved member and the fourth curved member along the length of the nerve. In some embodiments, the computational circuit is configured to determine a subset of nerve fibers that transmits the electrophysiological signal based on the electrophysiological signal detected by one or more of the first electrode pad, the second electrode pad, or the fifth electrode pad. In some embodiments, the subset of nerve fibers that transmits the electrophysiological signal is further determined based on data received from an interrogator. In some embodiments, the third electrode pads or the fourth electrode pad is configured to be selectively activated to emit the electrical pulse to a targeted subset of nerve fibers within the nerve.

In some embodiments, the computational circuit is configured to determine a direction or a velocity of the electrophysiological signal.

In some embodiments, the one or more electrode pads or the plurality of electrode pads is configured to be positioned outside of the nerve and in electrical communication with the nerve.

In some embodiments, the one or more electrode pads or the plurality of electrode pads is configured to be in contact with the epineurium of the nerve. In some embodiments, the one or more electrode pads or the plurality of electrode pads is configured to penetrate the epineurium of the nerve at one or more locations.

In some embodiments, the computational circuit is configured to downsample the detection signal or a component of the detection signal. In some embodiments, the computational circuit is configured to generate the stimulation signal based on a direction, a velocity, a frequency, an amplitude, or a waveform of a compound action potential or a subset of the compound action potential transmitted by the nerve or a subset of nerve fibers within the nerve.

In some embodiments, the stimulation signal comprises a timing, amplitude, frequency, or waveform of the electrical pulse emitted by the device.

Further described herein is a system comprising any one of the above devices and an interrogator configured to emit ultrasonic waves that power the device. In some embodiments, the interrogator is an external device. In some embodiments, the device comprises a non-transitory memory configured to store data based on the detected electrophysiological signal or the emitted electrical pulse, the ultrasonic transducer is configured to emit ultrasonic backscatter waves that encode at least a portion of the data, and the interrogator is configured to receive the ultrasonic backscatter waves. In some embodiments, the interrogator is further configured to decode the data.

Also described herein is a method of modulating neural activity, comprising: receiving ultrasonic waves at an ultrasonic transducer on a fully implanted closed-loop neuromodulation device; converting the ultrasonic waves into an electrical energy that powers the device; detecting, using the device, an electrophysiological signal transmitted by a targeted subset of nerve fibers within a nerve; generating, using the device, a stimulation signal based on the detected electrophysiological signal, emitting, using the device, an electrical pulse to the nerve based on the generated stimulation signal. In some embodiments, the electrical pulse is emitted to a second targeted subset of nerve fibers within the nerve.

Further described herein is a method of modulating neural activity, comprising: receiving ultrasonic waves at an ultrasonic transducer on a fully implanted closed-loop neuromodulation device; converting the ultrasonic waves into an electrical energy that powers the device; detecting, using the device, an electrophysiological signal transmitted by a nerve; generating, using the device, a stimulation signal based on the detected electrophysiological signal; emitting, using the device, an electrical pulse to a targeted subset of nerve fibers within the nerve based on the generated stimulation signal.

In some embodiments of the described methods, the method comprises storing the electrical energy on a battery within the device. In some embodiments, the method comprises storing data based on the detected electrophysiological signal or the emitted electrical pulse on a non-transitory memory within the device. In some embodiments, the data comprise a time stamp, a frequency, an amplitude, a waveform, a velocity, or a direction of the detected electrophysiological signal or the emitted electrical pulse.

In some embodiments of the described methods, the method comprises receiving data from an interrogator. In some embodiments, the data is encoded in ultrasonic waves transmitted by the interrogator. In some embodiments, the data received from the interrogator is stored on a non-transitory memory within the device.

In some embodiments of the described methods, the method comprises emitting an ultrasonic backscatter encoding at least a portion of the data stored on the non-transitory medium.

In some embodiments of the described methods, the method comprises determining a direction or a velocity of the detected electrophysiological signal.

In some embodiments of the described methods, the method comprises detecting or measuring a physiological condition. In some embodiments, the physiological condition comprises temperature, pH, pressure, heart rate, strain, and/or presence or amount of an analyte.

In some embodiments of the described methods, the method comprises downsampling the detected electrophysiological signal prior to generating the stimulation signal.

In some embodiments of the described methods, the stimulation signal is generated based on a frequency, amplitude, or waveform of the detected electrophysiological signal.

DETAILED DESCRIPTION

Figure 1:
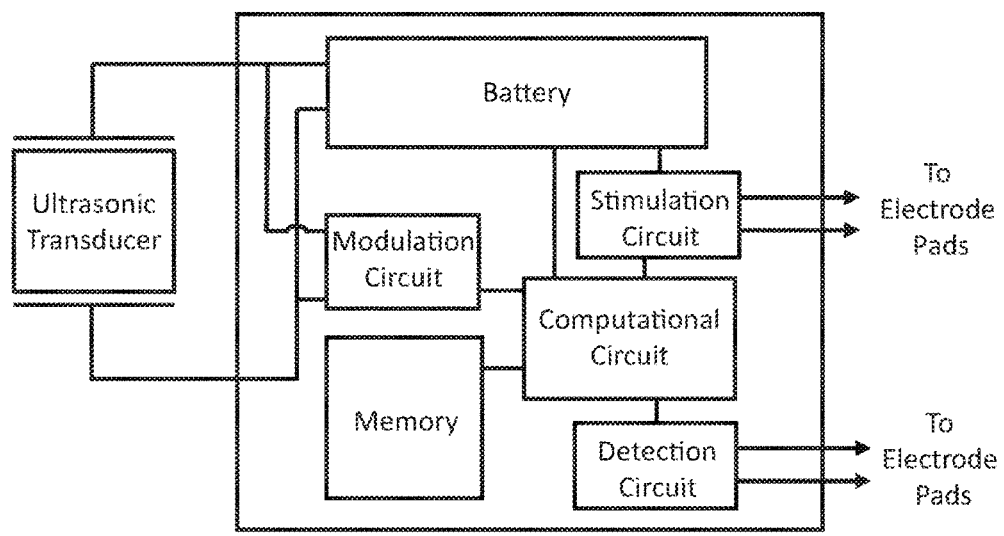
FIG. 1 illustrates a schematic of an exemplary body for the implantable closed-loop neuromodulation device described herein.

Described herein is an implantable closed-loop neuromodulation device that includes one or more curved members that at least partially circumscribe a nerve or other filamentous tissue, and include one or more electrode pads. The one or more electrode pads may be, for example, a plurality of electrode positioned along the curved member, or may be a curved electrode pad that at least partially circumscribes the nerve. The one or more curved member extends from a device body, which houses one or more ultrasonic transducers and a computational circuit for on-board computing of a stimulation pulse in response to the device detecting an electrophysiological signal. The one or more ultrasonic transducers can receive ultrasonic waves and convert energy from the ultrasonic waves into an electrical energy that can power the device. In some embodiments of the device, the electrical energy is stored in a battery, which is housed in the body of the device. The electrical energy powers the computational circuit, which is electrically connected to the electrode pads.

The computational circuit allows for on-board computing so that the device can emit an electrical pulse in response to an electrophysiological signal detected by the device. For example, an electrophysiological signal transmitted by the nerve can be detected by one or more (e.g., a plurality of) electrode pads on at least one of the one or more curved members of the device. The detection signal from the electrophysiological signal (which may be filtered, digitized, compressed, or otherwise processed) is received by the computational circuit, which generates a stimulation signal using the detection signal. The computational circuit can further operate the one or more electrode pads on at least one of the one or more curved members (which may be the same as or different from the one or more electrodes and/or curved member that detected the electrophysiological signal) to emit an electrical pulse based on the generated stimulation signal.

The curved members include one or more electrode pads, and are configured to at least partially circumscribe a nerve. For example, in some embodiments, the one or more curved members comprises a plurality of electrode pads positioned along the curved member, or the one or more curved members comprises a curved electrode pad that at least partially circumscribes the nerve. This configuration allows for targeted detection or stimulation of nerve activity. For example, a subset of electrode pads can be activated to target an electrical pulse to a subset of nerve fibers. Additionally, the device can detect an electrophysiological signal transmitted by a subset of nerve fibers by detecting the electrophysiological signal using the plurality of electrode pads and deciphering signals detected by the electrode pads to determine the transmitting subset. Therefore, the device can be configured to detect an electrophysiological signal from a targeted fascicle within the nerve or emit an electrical pulse to a targeted fascicle within the nerve.

Data related to the detected electrophysiological signal or the emitted electrical pulse can be stored on a non-transitory memory within the body of the device. The data can be transmitted to an external device, for example by encoding the data in ultrasonic backscatter waves emitted by the one or more ultrasonic transducers. The interrogator can transmit the ultrasonic waves to the device, for example the ultrasonic waves that are converted into the electrical energy by the one or more ultrasonic transducers of the device, and ultrasonic backscatter waves are emitted. The current flowing through the one or more ultrasonic transducers can be modulated to encode the data, which causes the ultrasonic backscatter waves emitted by the one or more ultrasonic transducers to encode the data.

Further described herein are methods of modulating neural activity. The method can include receiving ultrasonic waves at one or more ultrasonic transducers of an implanted closed-loop neuromodulation device and converting the ultrasonic waves into an electrical energy that powers the device. The device is used to detect an electrophysiological signal transmitted by a targeted signaling fascicle within a nerve. The device is then used to automatically generate a stimulation signals using the detected electrophysiological signal, and to emit an electrical pulse to the nerve based on the generated stimulation signal. The electrical pulse can be targeted to a targeted receiving fascicle within the nerve, which may be the same or different as the targeted signaling fascicle.

In another example, a method of modulating neural activity includes receiving ultrasonic waves at one or more ultrasonic transducers on a fully implanted closed-loop neuromodulation device, and converting the ultrasonic waves into an electrical energy that powers the device. The device is used to detect an electrophysiological signal transmitted by a nerve. The device is then used to generate a stimulation signal based on the detected electrophysiological signal, and emit an electrical pulse to a targeted receiving fascicle within the nerve based on the generated stimulation signal.

Definitions

As used herein, the singular forms "a," "an," and "the" include the plural reference unless the context clearly dictates otherwise.

Reference to "about" or "approximately" a value or parameter herein includes (and describes) variations that are directed to that value or parameter per se. For example, description referring to "about X" includes description of "X."

It is understood that aspects and variations of the invention described herein include "consisting" and/or "consisting essentially of" aspects and variations.

The terms "implantable" and "implanted" refer to an object being fully implantable or fully implanted in a subject such that no portion of the object breaches the surface of the subject.

The term "substantially" refers to 90% or more. For example, a curved member that substantially surrounds a cross-section of a nerve refers to a curved member that surrounds 90% or more of the cross-section of the nerve.

The term "subject" and "patient" are used interchangeably herein to refer to a vertebrate animal.

The terms "treat," "treating," and "treatment" are used synonymously herein to refer to any action providing a benefit to a subject afflicted with a disease state or condition, including improvement in the condition through lessening, inhibition, suppression, or elimination of at least one symptom, delay in progression of the disease or condition, delay in recurrence of the disease or condition, or inhibition of the disease or condition.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

It is to be understood that one, some or all of the properties of the various embodiments described herein may be combined to form other embodiments of the present invention. The section headings used herein are for organizational purposes only and are not to be construed as limiting the subject matter described.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

Implantable Closed-Loop Neuromodulation Device

The implantable neuromodulation device is a closed-loop device that can detect an electrophysiological signal from a nerve or a subset of nerve fibers, and emit an electrical pulse to the nerve or a subset of nerve fibers of the nerve (which may be the same subset or a different subset of nerve fibers from which the electrophysiological signal was detect) in response to the detected electrophysiological signal. In some embodiments, the implantable device detects a compound action potential (or a subset of the compound action potential) or other modulation of the electrophysiological signal, and the electrical pulse is emitted in response to the detected compound action potential (or subset thereof) or other modulation of the electrophysiological signal. Processing for the generation of the stimulation signal in response to the detected electrophysiological signal is performed by on-board computing using the computational circuit. Therefore, no external communication is needed to emit the electrical pulse in response to the detected electrophysiological signal.

The implantable closed-loop neuromodulation device includes one or more curved members that are configured to surround a nerve, and includes one or more (e.g., a plurality of) electrode pads that can detect an electrophysiological signal transmitted by the nerve and/or stimulate the nerve by emitting an electrical pulse. The device can include a plurality of curved members, with a first portion configured to detect the electrophysiological signal and a second portion configured to emit the electrical pulse. The curved members can include one or more (e.g., a plurality of) electrode pads on the inner surface of the curved members so that the electrode pads can be place in electrical communication with the never when implanted. For example, the curved members may include a plurality of electrode pads positioned along the curved member, which at least partially encompasses the nerve, or the curve members may include a curved electrode pad that at least partially circumscribes the nerve.

In some embodiments, the curved member substantially surrounds a cross-section of the nerve, with the electrode pads on an inner surface of the curved member and radially positioned around an axis along the length of the nerve. In this configuration, the electrode pads are circularly aligned with the cross-section of the nerve.

In some embodiments, the curved members include a plurality of electrode pads, which are radially positioned around an axis parallel to the length of the nerve, and are in electrical communication with the nerve when the implantable device is implanted. The curved members extend from a body, which include one or more ultrasonic transducers configured to receive ultrasonic waves and convert energy from the ultrasonic waves into an electrical energy, and a computational circuit electrically connected to the plurality of electrode pads. In some embodiments, the implantable device includes one, two, three, or more ultrasonic transducers.

The body of the device can house an integrated circuit, which includes the computational circuit, a modulation circuit, a detection circuit, and a stimulation circuit. The computational circuit is electrically connected to the plurality of electrode pads on the one or more curved members, and is configured to operate the electrode pads to emit an electrical pulse or detect an electrophysiological signal through the electrode pad. For example, the computational circuit is configured to receive a detection signal, generate a stimulation signal using the detection signal, and operate the plurality of electrode pads of at least one of the one or more curved members to emit an electrical pulse to the nerve based on the stimulation signal. The detection signal is based on the detected electrophysiological signal. Optionally, the detection signal may be further based on an additional physiological condition, for example temperature, pressure, heart rate, pH, or detection or concentration of an analyte. That is, the detection signal may optionally include a detected electrophysiological signal component and a detected physiological condition component. In some embodiments, the physiological condition is detected or measured using a sensor, which may be on the device, as further described herein.

The computational circuit can be a digital circuit, an analog circuit, or a mixed-signal integrated circuit. Exemplary computational circuits include a microprocessor, a finite state machine (FSM), a field programmable gate array (FPGA), and a microcontroller. In some embodiments, the integrated circuit includes a volatile memory, which can be accessed by the computational circuit.

In some embodiments, the computational circuit is configured to selectively activate the electrode pads within the plurality of electrode pads for targeted emission of the electrical pulse, as further described herein.

When the electrode pads signal are in electrical communication with the nerve, an electrophysiological signal transmitted by the nerve is detected by the electrode pads. The electrophysiological signal can include a baseline signal, and an action potential or compound action potential transmitted by the nerve results in modulation of the electrophysiological signal. A detection signal based on the electrophysiological signal detected by the electrode pads of the device is received by the computational circuit. The detection signal received by the computational circuit may be a raw electrophysiological signal detected by the device, or the electrophysiological signal may be processed (for example, amplified, digitized, and/or filtered) before being received by the computational circuit. In some embodiments, the detection signal includes a detected electrophysiological signal component and a physiological condition component, which can be together analyzed by the computational circuit to generate the stimulation signal. In some embodiments, the detection signal (or the detected electrophysiological signal component of the detection signal) is compressed by the computational circuit or other suitable circuitry within the device. Compression of the detection signal allows for faster and more energy efficient processing by the computational circuit, which allows for a more efficient closed-loop device. For example, the battery life of the on-board batter is longer with less data processing, and the time delay between receiving the detection signal and generating the stimulation signal is decreased. By way of example, compression of the detection signal can include down sampling the detection signal by retaining a portion of the data points in the detection signal. In another example, in some embodiments, the digital signal is compressed by identifying an electrophysiological signal spike above a baseline threshold, and using a timestamp associated with the electrophysiological signal spike as an input for the computational circuit. In some embodiments, the detection signal can be compared to a baseline signal, which may be an average signal (either electrophysiological signal, physiological condition, or both) detected for a period of time. The period of time can be, for example about 1 minute or more (such as about 2 minutes or more, about 5 minutes or more, about 10 minutes or more, about 15 minutes or more, about 30 minutes or more, or about 45 minutes or more). In some embodiments, the period of time is about 1 hour or less (such as about 45 minutes or less, about 30 minutes or less, about 15 minutes or less, about 10 minutes or less, about 5 minutes or less, or about 2 minutes or less. A detected deviation of the detection signal from the baseline signal can be used to trigger generation of the stimulation signal. For example, in some embodiments, if the amplitude of the modulated electrophysiological signal is above a baseline electrophysiological signal or above a predetermined amplitude threshold, the detected modulation is a signal input, which can be associated with one or more additional detected modulation in a temporal dimension. In some embodiments, the computational signal analyzes the non-compressed (e.g., raw) signal.

In some embodiments, the detected electrophysiological signal component of the detection signal includes, for example, a velocity, a direction, a frequency, an amplitude, a waveform of a compound action potential or a subset of the compound action potential (such as one or more action potential) transmitted by the nerve or a subset of nerve fibers within the nerve. The detected electrophysiological signal component may additionally or alternatively include information related to the subset of nerve fibers from which the electrophysiological signal was detected (that is, a location of the subset of nerve fibers within the nerve). This information can be used by the computational circuit, for example, to select a template detection signal and/or generate the stimulation signal.

A detection circuit can be included in the integrated circuit, and electrically connected to the plurality of electrode pads configured to detect the electrophysiological signal. The detection circuit can also optionally include an analog to digital converter (ADC), one or more filters, and/or one or more amplifiers.

Optionally, the implantable device further includes one or more sensors configured to measure or detect a physiological condition, such as an analyte, a pH, a temperature, a strain, a pulse rate, or a pressure (e.g., a blood pressure). The physiological condition detected by the implantable device can optionally be a component, in addition to the detected electrophysiological signal, of the detection signal received by the computational circuit. Therefore, the detection signal including the detected electrophysiological signal component and the additionally detected physiological condition component is used by the computational circuit to generate the simulation signal.

The detection signal can include one or more detected signals (electrophysiological signal and/or physiological condition), which may be detected at different time points. A time stamp for the signals can be associated with the detected signal, and can be included in the detection signal for analysis by the computational circuit. For example, a detection signal that includes a predetermined number of detected electrophysiological signal spikes within a period of time can result in the generation of a stimulation signal by the computational circuit.

The computational circuit can analyze the detection signal to generate a stimulation signal using the detection signal. The analysis can include, for example, identifying a modulation of the detection signal (such as a modulation of the detected electrophysiological signal, the detected physiological condition, or both), which can act as a trigger for generation of the stimulation signal. The modulation of the electrophysiological signal can indicate, for example, a compound action potential or a component of the compound action potential (e.g., one or more action potentials) that is being transmitted by the nerve. The stimulation signal can be generated using a mathematical relationship between the detection signal and the stimulation signal. Thus, the computational circuit can input the detection signal into the mathematical relationship to generate the stimulation signal. The mathematical relationship can be determine, for example, using machine learning or can be a pre-selected mathematical relationship. In some embodiments, the computational circuit uses a digital logic, an analog logic, an artificial neural network, a convolutional neural network (CNN), or neuromorphic computing to detect deviation of the detection signal from a baseline signal.

In some embodiments, generating the stimulation signal can include comparing the detection signal (which may include a detected electrophysiological signal component and/or a detected physiological signal component) to a template detection signal, and the stimulation signal is generated based on the variance or similarity between the detection signal and the template detection signal. One or more template detection signals can be stored, for example, on a non-transitory memory in the body of the device. The computational circuit can use, for example, a digital logic, an analog logic, an artificial neural network, a convolutional neural network (CNN), or neuromorphic computing to detect the variance or similarity between the detected electrophysiological signal and the template electrophysiological signal.

The stimulation signal generated by the computational circuit can include information about the electrical pulse to be emitted by the device, such as amplitude, frequency, waveform, or targeted location (i.e., subset of nerve fibers) within the nerve. In some embodiments, one or more template pulses are stored on a non-transitory memory within the device (e.g., within the body of the device). The computational circuit can generate the stimulation signal by retrieving a template pulse from the non-transitory memory using the detection signal. For example, generating the stimulation signal can include analyzing the detection signal, retrieving a template pulse from the non-transitory memory based on the analyzed detection signal, and generating the stimulation signal based on the retrieved template pulse. Depending on whether or how the detection signal is modulated from a baseline or compares to a template detection signal can determine which template pulse is retrieved or stimulation signal generated.

The integrated circuit can include a stimulation circuit, which is operated by the computational circuit and is electrically connected to electrode pads that emit the electrophysiological pulse. The stimulation circuit can include a stimulating capacitor, which can be charged by the battery or electrical energy converted from the ultrasonic waves by the one or more ultrasonic transducers. The status of the stimulating capacitor, for example capacitor charge, can be determined by the computational circuit. Optionally, the status of the stimulating capacitor is recorded on the non-transitory memory or encoded in ultrasonic backscatter waves through the modulation circuit operated by the computational circuit.

The computational circuit operates the electrode pads of at least one of the one or more curved members to emit an electrical pulse to the nerve based on the stimulation signal.

For example, the stimulation signal can include a pulse amplitude, frequency, and/or waveform, and the computational circuit controls the electrode pads to emit the pulse in accordance with the stimulation signal. The device can include a capacitor (i.e., a stimulating capacitor), such as within the body of the device, which stores an electrical charge and is controlled by the computational circuit. The computational circuit controls the capacitor to emit the electrical pulse through the electrode pads. In some embodiments, the computational circuit is configured to determine a stimulating capacitor status, such as a charge of the capacitor. The capacitor status can be stored in the non-transitory memory and/or encoded in ultrasonic backscatter waves.

In some embodiments, the implantable device further includes a battery configured to receive the electrical energy from the one or more ultrasonic transducers and power the computational circuit. Inclusion of the battery allows the computational circuit to function without an external power source, including detecting an electrophysiological signal or emitting an electrical pulse to the nerve. The battery can be contained within the body of the implantable device. The battery can be, for example, a rechargeable electrochemical battery. The energy stored by the battery can power the device, for example when the one or more ultrasonic transducers are not receiving ultrasonic waves. The battery can be charged by transmitting ultrasonic waves to the device using an interrogator which are received by the one or more ultrasonic transducers. The one or more ultrasonic transducers convert the ultrasonic waves into an electrical energy, and are electrically connected to the battery. In this manner, the electrical energy charges the battery of the device.

The implantable closed-loop neuromodulation device can also include a non-transitory memory configured to store data based on an electrophysiological signal detected by the device or an electrical pulse emitted by the device. The data can include, for example, a time stamp, a velocity, a direction, an amplitude, a frequency, or a waveform of a detected action potential or compound action potential; and/or a time stamp, an amplitude, a frequency, or a waveform of an electrical pulse emitted by implantable device. In some embodiments, the non-transitory memory can store data related to a detected physiological condition (such as temperature, pH, pressure, heart rate, strain, and/or presence or amount of an analyte). The data stored on the non-transitory memory may be acquired over a period of time (such as about 1 minute or more, about 5 minutes or more, about 10 minutes or more, about 15 minutes or more, about 30 minutes or more, about 45 minutes or more, about 1 hour or more, about 2 hours or more, about 4 hours our more, about 6 hours or more, about 8 hours or more, about 12 hours or more, or about 24 hours or more).

In some embodiments, the device is configured to encode at least a portion of the data stored on the non-transitory memory in ultrasonic backscatter waves. This allows the data to be wirelessly transmitted to an interrogator, which may be implanted or external to the subject. Data encoded in the ultrasonic backscatter waves can be compressed. Compression may be used, for example, for efficient transmission of the data due to bandwidth limits between the implantable device and the interrogator. By way of example, data compression can include transmitting down sampled data from the detection signal, processed data, or one or more features in the signal (such as a time stamp of a detected electrophysiological signal spike). The implantable device can include a modulation circuit electrically connected to the one or more ultrasonic transducers. Upon receiving ultrasonic waves from an interrogator, a current is generated that flows through the one or more ultrasonic transducers and the modulation circuit. The computational circuit can operate the modulation circuit to encode data stored on the non-transitory memory onto the current. The one or more ultrasonic transducers of the device emit ultrasonic backscatter waves, which can encode the data encoded into the current. The ultrasonic backscatter waves can be received by an interrogator, which may be the same or different as the interrogator transmitting the ultrasonic waves to the implantable device, and the data encoded on the ultrasonic backscatter waves can be deciphered.

The non-transitory memory can also be used to store data transmitted to the device from an interrogator. The interrogator can transmit data (such as temperature data, or data related to some other physiological condition, such as an analyte concentration in the blood or interstitial fluid of a subject), which is received by the implantable device and can be stored on the non-transitory memory. The data can be transmitted, for example, through ultrasonic waves that encode the data. The interrogator can transmit the ultrasonic waves, which are received by the ultrasonic transducer of the device and deciphered by the computational circuit.

The non-transitory memory can store one or more instructions for operating the device, which can be executed using the computational circuit. For example, the non-transitory memory can include instructions for receiving a detection signal based on detected electrophysiological signal; generating a stimulation signal using the detection signal; and operating the plurality of electrode pads of at least one of the one or more curved members to emit an electrical pulse to the nerve based on the stimulation signal. In some embodiments, the non-transitory memory includes instructions for selectively activating one or more electrodes with the plurality of electrodes for targeted emission of the electrical pulse. In some embodiments, the non-transitory memory comprises instructions for analyzing a detected electrophysiological signal (and, optionally, a measured physiological condition), for example by determining a variance in the detected electrophysiological signal (and/or physiological condition) compared to a baseline electrophysiological signal (and/or physiological condition). In some embodiments, the non-transitory memory comprises instructions for comparing the detected electrophysiological signal (and/or physiological condition) to a template electrophysiological signal (and/or physiological condition).

FIG. 1 illustrates a schematic of an exemplary body for the implantable closed-loop neuromodulation device described herein. The body includes an ultrasonic transducer electrically connected to a battery and a modulation circuit. The battery is electrically connected to and powers a computational circuit, which is electrically connected to a non-transitory memory and the modulation circuit. The computational circuit is also electrically connected and is configured to operate the electrodes on the curved member or curved members of the device through a stimulation circuit or a detection circuit. Ultrasonic waves are received by the ultrasonic transducer, which converts the energy from the ultrasonic waves into an electrical energy that charges the battery. The electrodes on the device are configured to detect an electrophysiological signal, and a detection signal based on the electrophysiological signal is received by the computational circuit. The detection signal received by the computational circuit may be processed (for example, amplified, digitized, and/or filtered) by the detection circuit before being received by the computational circuit. Optionally, the computational circuit accesses the non-transitory memory to store data related to the detected electrophysiological signal. The computational circuit can generate a stimulation signal based on the detection signal, and operate the electrodes to emit an electrical pulse to the nerve based on the stimulation signal. Optionally, the computational circuit accesses the non-transitory memory to store data related to the stimulation signal or electrical pulse emitted to the nerve. Data stored on the non-transitory memory can be wirelessly transmitted through ultrasonic backscatter waves emitted by the ultrasonic transducer. The ultrasonic transducer receives ultrasonic waves, and generates a current that flows through the modulation circuit. The computational circuit accesses the memory and operates the modulation circuit to modulate the current flowing through the modulation circuit to encode the data. The ultrasonic backscatter waves emitted by the ultrasonic transducer thereby encode the data.

In some embodiments, the body includes a housing, which can include a base, one or more sidewalls, and a top. The housing can enclose the one or more ultrasonic transducers and the integrated circuit (which includes the computational circuit, the non-transitory memory, the battery, the modulation circuit, a detection circuit, and/or a stimulation circuit (which can include a stimulating capacitor)). The hosing may be sealed closed (for example by soldering or laser welding) to prevent interstitial fluid from coming in contact with the ultrasonic transducer(s) and/or the integrated circuit. The housing is preferably made from a bioinert material, such as a bioinert metal (e.g., steel or titanium) or a bioinert ceramic (e.g., titania or alumina). The housing (or the top of the housing) may be thin to allow ultrasonic waves to penetrate through the housing. In some embodiments, the thickness of the housing is about 100 micormeters (μm) or less in thickness, such as about 75 μm or less, about 50 μm or less, about 25 μm or less, or about 10 μm or less. In some embodiments, the thickness of the housing is about 5 μm to about 10 μm, about 10 μm to about 25 μm, about 25 μm to about 50 μm, about 50 μm to about 75 μm, or about 75 μm to about 100 μm in thickness.

The body of the implantable device is relatively small, which allows for comfortable and long-term implantation while limiting tissue inflammation that is often associated with implantable devices. In some embodiments, the longest dimension of the body of the device is about 10 mm or less, such as about 5 mm to about 9 mm, or about 6 mm to about 8 mm.

In some embodiments, the body comprises a material, such as a polymer, within the housing. The material can fill empty space within the housing to reduce acoustic impedance mismatch between the tissue outside of the housing and within the housing. Accordingly, the body of the device is preferably void of air or vacuum.

One or more ultrasonic transducers of the implantable device can be a micro-machined ultrasonic transducer, such as a capacitive micro-machined ultrasonic transducer (CMUT) or a piezoelectric micro-machined ultrasonic transducer (PMUT), or can be a bulk piezoelectric transducer. Bulk piezoelectric transducers can be any natural or synthetic material, such as a crystal, ceramic, or polymer. Exemplary bulk piezoelectric transducer materials include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate (Na$_2$WO$_3$), bismuth ferrite (BiFeO$_3$), polyvinylidene (di)fluoride (PVDF), and lead magnesium niobate-lead titanate (PMN-PT).

In some embodiments, the bulk piezoelectric transducer is approximately cubic (i.e., an aspect ratio of about 1:1:1 (length:width:height). In some embodiments, the piezoelectric transducer is plate-like, with an aspect ratio of about 5:5:1 or greater in either the length or width aspect, such as about 7:5:1 or greater, or about 10:10:1 or greater. In some embodiments, the bulk piezoelectric transducer is long and narrow, with an aspect ratio of about 3:1:1 or greater, and where the longest dimension is aligned to the direction of the ultrasonic backscatter waves (i.e., the polarization axis). In some embodiments, one dimension of the bulk piezoelectric transducer is equal to one half of the wavelength (k) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 µm to about 1000 µm (such as about 40 µm to about 400 µm, about 100 µm to about 250 µm, about 250 µm to about 500 µm, or about 500 µm to about 1000 µm). In some embodiments, the height of the piezoelectric transducer is about 5 mm or less (such as about 4 mm or less, about 3 mm or less, about 2 mm or less, about 1 mm or less, about 500 µm or less, about 400 µm or less, 250 µm or less, about 100 µm or less, or about 40 µm or less). In some embodiments, the height of the piezoelectric transducer is about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in length.

In some embodiments, the one or more ultrasonic transducers have a length of about 5 mm or less such as about 4 mm or less, about 3 mm or less, about 2 mm or less, about 1 mm or less, about 500 µm or less, about 400 µm or less, 250 µm or less, about 100 µm or less, or about 40 µm or less) in the longest dimension. In some embodiments, the ultrasonic transducer has a length of about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in the longest dimension.

The ultrasonic transducer is connected two electrodes to allow electrical communication with the computational circuit. The first electrode is attached to a first face of the transducer and the second electrode is attached to a second face of the transducer, wherein the first face and the second face are opposite sides of the transducer along one dimension. In some embodiments, the electrodes comprise silver, gold, platinum, platinum-black, poly(3,4-ethylenedioxythiophene (PEDOT), a conductive polymer (such as conductive PDMS or polyimide), or nickel. In some embodiments, the axis between the electrodes of the transducer is orthogonal to the motion of the transducer.

The curved members of the device extend from the body of the device to at least partially circumscribe a nerve, and one or more electrode pads are included on the curved members. The electrode pads can be configured to be in electrical communication with the nerve, for example to detect an electrophysiological signal transmitted by the nerve and/or emit one or more electrical pulses to the nerve. For example, the one or more electrode pads may be on an inner surface of the curved members, and the one or more curved members may engage the nerve or filamentous tissue that includes the nerve (such as a blood vessel connected to the nerve) to secure the device to the nerve or other filamentous tissue and position the electrode pads.

The curved members may be flexible, which allows for deformation of the curved members during implantation of the device. For example, the cured members may be flexed outwardly while the device is being positioned on the nerve. Release of the curved members allows the curved members to wrap around the nerve or filamentous tissue containing the nerve. Optionally, the curved member includes two portions that are bridged by the body of the device.

The electrode pad (or pads) may, for example, be configured to at least partially surround an axis parallel to the length of a nerve, or a plurality of electrode pads may be configured to be radially positioned around the axis parallel to the length of the nerve. The device may include curved members with different electrode pad configurations. For example, in some embodiments, a device may include one or more curved members with a plurality of electrode pads positioned along the curved member, and one or more curved members with a curved electrode pad that at least partially circumscribes the nerve.

In some embodiments, the curved members that extend from the body of the device each include a plurality of electrode pads configured to be radially positioned around the nerve (i.e., around an axis that runs parallel through the center of and along the length of the nerve) and in electrical communication with the nerve. The curved members extend away from the body before curving toward the body as the curved members extend below the body, resulting in a ring-like structure that results in the curved members sustainably circumscribing a cross-section of the nerve or filamentous tissue that includes the nerve (such as a blood vessel connected to the nerve). In some embodiments, the curved members make a single loop around the cross-section of the nerve. Once in position, the electrode pads of a given curved member are within the same cross-sectional location relative to the nerve. A space within the curved member can be included to allow the device to be implanted on the nerve. The curved members can be flexible, which allows for deformation of the curved members during implantation of the device. The cured members can be flexed outwardly while the device is being positioned on the nerve. Release of the curved members allows the curved members to wrap around the nerve or filamentous tissue containing the nerve. Optionally, the curved member includes two portions that are bridged by the body of the device.

Figure 2A:
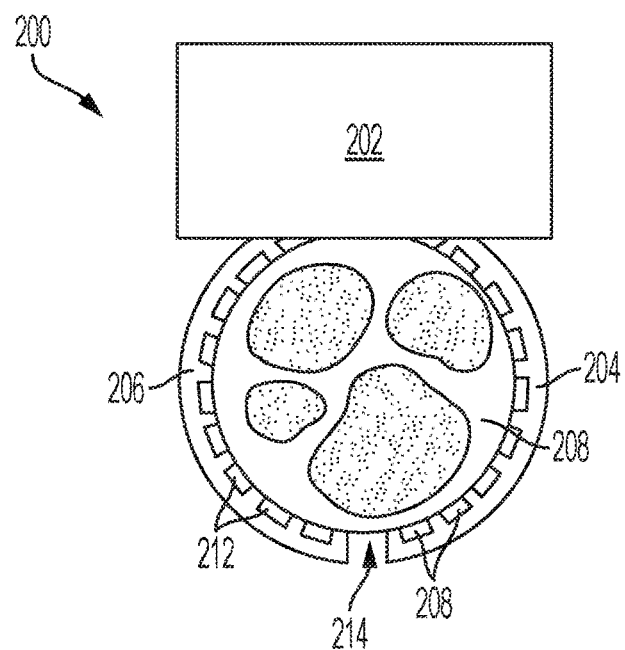
FIG. 2A illustrates an exemplary implantable neuromodulation device with two curved members extending from a body and implanted on a nerve (shown as a cross-sectional plane). The curved members partially circumscribe the nerve, and include a plurality of electrode pads positioned along the curved member.

FIG. 2A illustrates an exemplary embodiment of a device with a first curved member and a second curved member that each partially circumscribe a nerve to engages the nerve. The device 200 includes a body 202 attached to a first curved member 204 and a second curved member 206. A plurality of electrodes 208 on the inner surface of the first curved member 204 is positioned along the first curved member, 204, and plurality of electrodes 212 is positioned along the second curved member 206. In the illustrated example, the first curved member 204 and the second curved member 206 are flexible members that are separated by a gap (i.e., a separation) 214. In this configuration, the first curved member 204 and the second curved member 206 can be flexed outwardly (thereby widening the gap 214) to allow the nerve 208 to be positioned within the space between the curved members, and the curved members can be released so that the curved members wrap around the nerve.

Figure 2B:
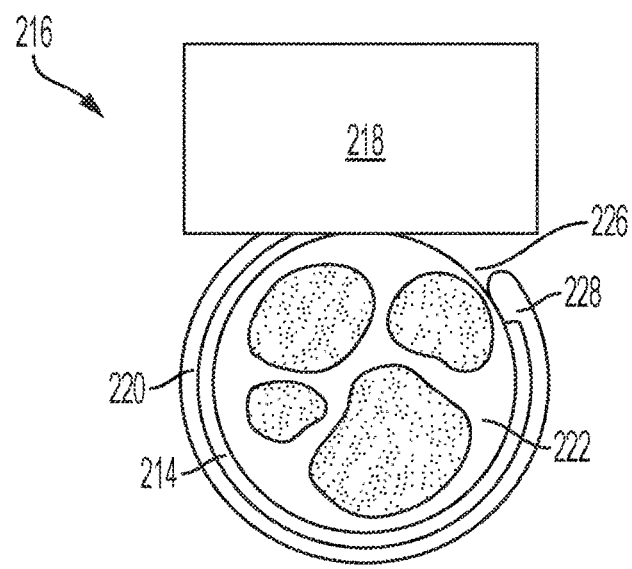
FIG. 2B illustrates an exemplary implantable neuromodulation device with a curve member that substantially circumscribes a nerve (shown as a cross-sectional plane). The curve member includes an electrode pad that partially circumscribes the nerve, although not to the same extent as the curved member.

FIG. 2B illustrates another exemplary embodiment of a device with a curved member that engages a nerve. The device 216 includes a body 218 and a curved member 220 that substantially circumscribes a nerve 222. The inner surface of the curved member 220 includes a curved electrode pad 224 that circumscribes the nerve 222. The curved member 220 may be flexible, and a space 226 may be present between the body 218 and the end 228 of the curved member 220 (or between a first curved member a second curved member). The curved member may be flexed outwardly to allow the nerve 222 to be positioned within the space formed by the curved member, and the curved member may be released so that the curved member wraps around the nerve 222.

The configurations of the curved members and electrode pads shown in FIG. 2A and FIG. 2B may be combined. For example, a device may include a curved member as shown in FIG. 2A and a curved member as shown in FIG. 2B. In another embodiment, the device may include first and second curved members (as shown in FIG. 2A) and a curved electrode (as shown in FIG. 2B). In another embodiment, the device may include a curved member that substantially surrounds the nerve (e.g., as shown in FIG. 2B) with a plurality of electrode positioned along the curved member (e.g., as shown in FIG. 2A).

The size, shape, and spacing of the one or more curved members on the device can depend on the type and size of tissue that device engages. In some embodiments, the two or more curved members are spaced by about 0.25 mm or more (such as about 0.5 mm or more, about 1 mm or more, about 2 mm or more, about 3 mm or more, about 4 mm or more, about 5 mm or more, about 6 mm or more, or about 7 mm or more). In some embodiments, the two or more curved members are space by about 8 mm or less (such as about 7 mm or less, about 6 mm or less, about 5 mm or less, about 4 mm or less, about 3 mm or less, about 2 mm or less, about 1 mm or less, or about 0.5 mm or less). By way of example, the two or more curved members can be spaced by about 0.25 mm to about 0.5 mm, about 0.5 mm to about 1 mm, about 1 mm to about 2 mm, about 2 mm to about 3 mm, about 3 mm to about 4 mm, about 4 mm to about 5 mm, about 5 mm to about 6 mm, about 5 mm to about 7 mm, or about 7 mm to about 8 mm apart. The width of the curved members can also vary depending on the application of the device or the tissue engaged by the device. In some embodiments, the width of the curved member is about 100 µm or more (such as about 150 µm or more, about 250 µm or more, about 500 µm or more, about 1 mm or more, or about 1.5 mm or more). In some embodiments, the width of the curved member is about 2 mm or less (such as about 1.5 mm or less, about 1 mm or less, about 500 µm or less, about 250 µm or less, or about 150 µm or less. In some embodiments, the width of the curved members is about 100 µm to about 2 mm (such as about 100 µm to about 150 µm, about 150 µm to about 250 µm, about 250 µm to about 500 µm, about 500 µm to about 1 mm, about 1 mm to about 1.5 mm, or about 1.5 mm to about 2 mm). The inner surface of the curved members form a cylindrical space through which the nerve and/or filamentous tissue passes. The diameter of the cylindrical space formed by the curved members depends on the target nerve and/or filamentous tissue that the implantable device will engage. In some embodiments, the one or more curved members of the device form a cylindrical space with a diameter of about 50 µm to about 15 mm (for example, about 50 µm to about 100 µm, about 100 µm to about 250 µm, about 250 µm to about 500 µm, about 500 µm to about 1 mm, about 1 mm to about 1.5 mm, about 1.5 mm to about 2.5 mm, about 2.5 mm to about 5 mm, about 5 mm to about 10 mm, or about 10 mm to about 15 mm).

The one or more curved members may be configured to at least partially circumscribe the nerve or other filamentous tissue. For example, the curved member may be configured to circumscribe at least 25%, at least 33%, at least 50%, at least 66%, at least 75%, at least 90%, or at least 100% (for example, the curve member may completely surround the nerve or filamentous tissue, or may include more than one complete loop around the nerve or filamentous tissue) of the nerve or filamentous tissue. Similarly, the one or more curved electrode pads, may circumscribe at least 25%, at least 33%, at least 50%, at least 66%, at least 75%, at least 90%, or at least 100% of the nerve, and the portion of the nerve circumscribed by the curved electrode pad may be the same or less than the portion of the nerve circumscribed by the curved member. The plurality of electrode pads positioned on the curved member may be positioned along the full length of the curved member or a portion of the length of the curved member.

In some embodiments, the implantable device includes one or more additional securing members configured to secure the implantable device to the filamentous tissue. Such securing members can include, for example, loops for suturing the implantable device to anatomical structure (such as the filamentous tissue or nerve, or other tissue surrounding the filamentous tissue or nerve), pins, or clamps. For example, the implantable device can be sutured to the filamentous tissue or nerve, or tissue surrounding the filamentous tissue or nerve, to limit movement of the implantable device once implanted.

The curved members of the implantable device can comprise a metal, metal alloy, ceramic, silicon, or a non-polymeric material. The curved members may be flexible, and are preferably sprung such that the curved members can be positioned around the nerve and/or filamentous tissue. In some embodiments, the one or more curved members or a portion of the one or more curved members are coated with an elastomeric coating or a non-elastomeric coating, which is preferably bioinert, such as polydimethylsioloxane (PDMS), a silicone, a urethane polymer, a poly(p-xylyene) polymer (such as a poly(p-xylyene) polymer sold under the tradename PARYLENE®), or a polyimide. The one or more curved members each include a plurality of electrode pads on an inner surface of the curved members. In some embodiments, the electrode pads on the inner surface of the curved members are not coated with the elastomeric coating or the non-elastomeric polymer coating, although may be coated with a conductive material (e.g., electroplated with a PEDOT polymer or a metal to improve electrical characteristics of the electrode pad). Accordingly, in some embodiments, only the outer surface of the curved member is coated with the coating. Optionally, the coating further coats the housing of the body.

The one or more curved members can hold the implantable device in place on the nerve and/or filamentous tissue. In some embodiments, the one or more curved members allow for some rotational movement of the implantable device on the nerve and/or filamentous tissue. In some embodiments, the one or more curved members grip the nerve and/or filamentous tissue by exerting an inward pressure on the nerve and/or filamentous tissue. The amount of inward pressure exerted by the one or more curved members can be determined based on the size and curvature of the curved members, as well as by the spring constant of the curved members. The inward pressure should be sufficient to hold the implantable device in place while the tissue heals after insertion, but not so high that the epineurium or vascular walls that contact the curved members are damaged. In some embodiments, the inward pressure on the nerve or filamentous tissue is about 1 MPa or less (such as about 0.7 MPa or less, about 0.5 MPa or less, or about 0.3 MPa or less). In some embodiments, the inward pressure on the nerve or filamentous tissue is about 0.1 MPa to about 1 MPa (such as about 0.1 MPa to about 0.3 MPa, about 0.3 MPa to about 0.5 MPa, about 0.5 MPa to about 0.7 MPa, or about 0.7 MPa to about 1 MPa).

The plurality of electrode pads on each curved member is positioned on an inner surface of the curved member (that is, the surface of the curved surface that is configured to interface with the nerve and/or filamentous tissue). In some embodiments, the plurality of electrode pads include 2, 3, 4, 5, 6, 7, 8, 9, 10, 11, 12, 13, 14, 15, 16, 17, 18, 19, 20, or more electrode pads, such as between about 3 and about 50 electrode pads, between about 3 and about 5 electrode pads, between about 5 and about 10 electrode pads, between about 10 and about 25 electrode pads, or between about 25 and about 50 electrode pads. In some embodiments, the electrode pads within the plurality of electrode pads can be selectively activated by the computational circuit, which allows for targeted electrical pulse emission, as further described herein.

The electrode pads can include any suitable conductive material, such as one or more of (or an alloy of one or more of) tungsten, platinum, palladium, gold, iridium, niobium, tantalum, or titanium. The material of the detecting electrode pads and the stimulating electrode pads may be the same or different. The size and shape of the electrode pads may also be the same or different. For example, electrode pads on a given curved members may be of the same or different size, and electrode pads on different curved members may be of the same or different size.

The electrode pads of the implantable device are positioned by the curved members to be in electrical communication with the nerve. In some embodiments, the electrode pads are not in direct contact with the nerve (for example outside and not indirect contact with the nerve), but are in electrical communication with the nerve. In some embodiments, the electrode pads are positioned within about 2 mm (within about 1.8 mm, within about 1.6 mm, within about 1.4 mm, within about 1.2 mm, within about 1.0 mm, within about 0.8 mm, within about 0.6 mm, within about 0.4 mm, or within about 0.2 mm of the nerve. In some embodiments, the plurality of electrode pads is configured to penetrate the epineurium of the nerve at one or more locations. For example, the electrode pads can be needle-shaped, which allows for penetration of the epineurium. In some embodiments, the electrode pads directly contact the nerve, for example the epineurium of the nerve.

In some embodiments, one or more of the curved members on the device is configured to detect the electrophysiological signal transmitted by the nerve. In some embodiments, one or more or more curved members on the device are configured to emit the electrical pulse. The one or more curved members that are configured to detect the electrophysiological signal transmitted by the nerve may be the same or different from the one or more curved members that are configured to emit the electrical pulse. For example, in some embodiments the device includes a first curved member that includes a first plurality of electrode pads configured to detect the electrophysiological signal transmitted by the nerve, and a second curved member that includes a second plurality of electrode pads configured to emit the electrical pulse to the nerve. In some embodiments, the device includes two, three, four, five, six, seven, eight or more curved members. In some embodiments, the device includes one, two, three, four, five, six, seven, eight or more curved members configured to detect the electrophysiological signal transmitted by the nerve, and one, two, three, four, five, six, seven, eight or more curved members configured to emit the electrical pulse. In some embodiments, the curved members having electrode pads configured to detect the electrophysiological signal and the curved members having electrode pads configured to emit the electrical pulse are separate curved members to allow for concurrent detection of the electrophysiological signal and emission of the electrical pulse.

Multiple curved members can be positioned along the length of the nerve. This configuration allows for electrophysiological signal detection and/or emission of an electrical pulse, which may be target to a subset of nerve fibers within the nerve, at different points along the length of the nerve. By detecting an electrophysiological signal at two or more positions along the length of the nerve, the computational circuit can determine a direction and/or velocity of the electrophysiological signal transmitted by the nerve. To determine direction of the electrophysiological signal (e.g., an efferent signal or an afferent signal), the computational circuit can use on a first time stamp of the electrophysiological signal detected by a first curved member and a second time stamp of the electrophysiological signal detected by the second curved member. To determine the velocity of the electrophysiological signal, the computational circuit can further use the known distance between the first curved member and the second curved member. In some embodiments, the identity of the electrophysiological signal detected by the electrode pads of the first curved member and the second curved member is confirmed by comparing one or more electrophysiological signal features (e.g., amplitude, frequency, or waveform) detected by the electrode pads on the first curved member and the electrode pads of the second curved member.

The implantable device can also include two or more curved members comprising a plurality of electrodes configured to emit an electrical pulse or an electrical pulse train. The two or more curved members can be positioned at different locations along the length of the nerve, and are configured to emit an electrical pulse at the different positions. The electrical pulse emitted by the two or more different curved members may be the same or different, and may be targeted to the same or different subset of curved members within the nerve. For example, a first electrode pad (or a first plurality of electrode pads) on a first curved member can emit an electrical pulse configured to block transmission of an electrophysiological signal by a first subset of nerve subset of nerve fibers, and a second electrode pad (or second plurality of electrode pads) on a second curved member can be configured to emit an electrical pulse that stimulates a second subset of nerve fibers. In some embodiments, the first subset of nerve fibers can be, for example, efferent nerve fibers, while the second subset of nerve fibers is afferent nerve fibers. In other embodiments the first subset of nerve fibers are afferent nerve fibers, and the second subset of nerve fibers are efferent nerve fibers. By blocking transmission of an electrophysiological signal in a first subset of nerve fibers and stimulating a second subset of nerve fibers, off-target effects of the stimulation are minimized. In another example, the one or more electrode pads within the first plurality of electrode pads on the first curved member and one or more electrode pads within the second plurality of electrode pads on the second curved members can be operated for bipolar stimulation along the length of the nerve. In a further example, the plurality of electrodes on the first curved member and the plurality of electrodes on the second curved member can each emit a coordinated electrical pulse (that is, the electrical pulses emitted by the separate pluralities of electrodes are coordinated with each other), which can be used for specific focal stimulation.

By way of example, in some embodiments the device comprises a first curved member comprising a first plurality of electrode pads and a second curved member comprising a second plurality of electrode pads, wherein the first plurality of electrodes and the second plurality of electrodes are each configured to be radially positioned around the axis parallel to the length of the nerve at different positions along the length of the nerve. In some embodiments, the first plurality of electrode pads and the second plurality of electrode pads are configured to detect the electrophysiological signal transmitted by the nerve. In some embodiments, the device optionally further comprises a third curved member comprising a third plurality of electrode pads, wherein the third plurality of electrode pads is configured to be radially positioned around the axis parallel to the length of the nerve at a position between the first curved member and the second curved member along the length of the nerve.

As another example, in some embodiments, the device includes a first curved member comprising a first plurality of electrode pads and a second curved member comprising a second plurality of electrode pads, wherein the first plurality of electrodes and the second plurality of electrodes are each configured to be radially positioned around the axis parallel to the length of the nerve at different positions along the length of the nerve, wherein the first plurality of electrode pads or the second plurality of electrode pads are configured to emit the electrical pulse to the nerve. In some embodiments, the electrode pads within the first plurality of electrode pads and/or the second plurality of electrode pads are configured to be selectively activated to emit the electrical pulse to the nerve for example by targeting a subset of nerve fibers within the nerve.

In another example, in some embodiments, the device includes a first curved member comprising a first plurality of electrode pads, and a second curved member comprising a second plurality of electrode pads, the first plurality of electrode pads and the second plurality of electrode pads configured to detect the electrophysiological signal transmitted by the nerve; and a third curved member comprising a third plurality of electrode pads, and a fourth curved member comprising a fourth plurality of electrode pads, the third plurality of electrode pads and the fourth plurality of electrode pads configured to emit the electrical pulse; wherein the first plurality of electrodes, the second plurality of electrodes, the third plurality of electrodes, and the fourth plurality of electrodes are each configured to be radially positioned around the axis parallel to the nerve at different positions along the length of the nerve. Optionally, the third curved member and the fourth curved member are positioned between the first curved member and the second curved member along the length of the nerve. In some embodiments, the device further includes a fifth curved member comprising a fifth plurality of electrode pads configured to detect the electrophysiological signal or emit the electrical pulse. The fifth curved member is optionally positioned between the third curved member and the fourth curved member along the length of the nerve. In some embodiments, the first plurality of electrode pads, the second plurality of electrode pads, the third plurality of electrode pads, or the fourth plurality of electrode pads and/or the fifth plurality of electrode pads are configured to be selectively activated to emit the electrical pulse.

Figure 3A:
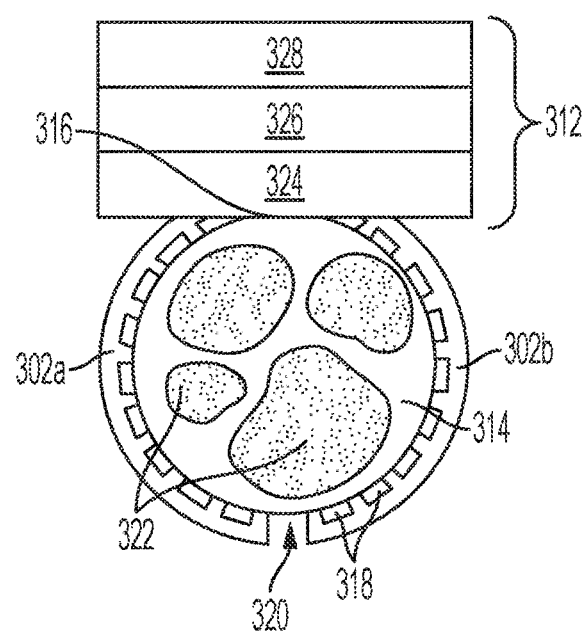
FIG. 3A illustrates a front view of an exemplary implantable closed-loop neuromodulation device with five curved members extending from a body and implanted on a nerve.
Figure 3B:
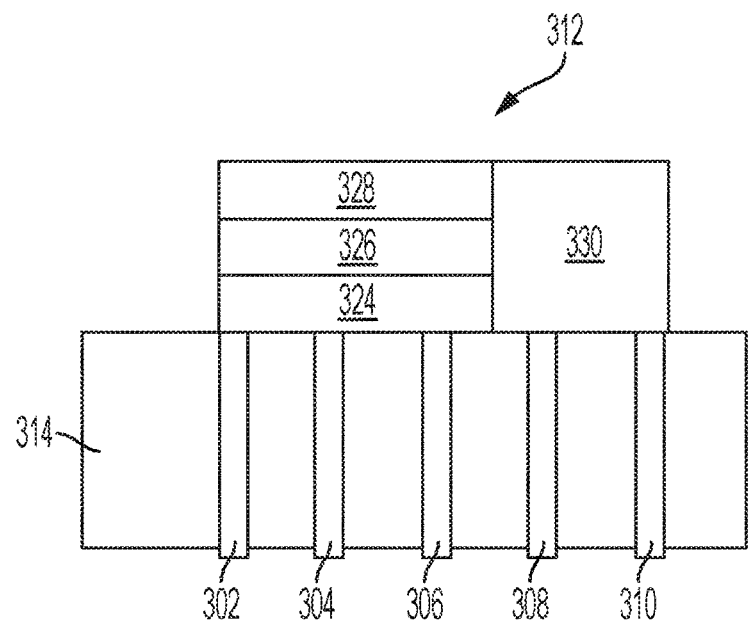
FIG. 3B illustrates a side view of the device illustrated in FIG. 3A.
Figure 3C:
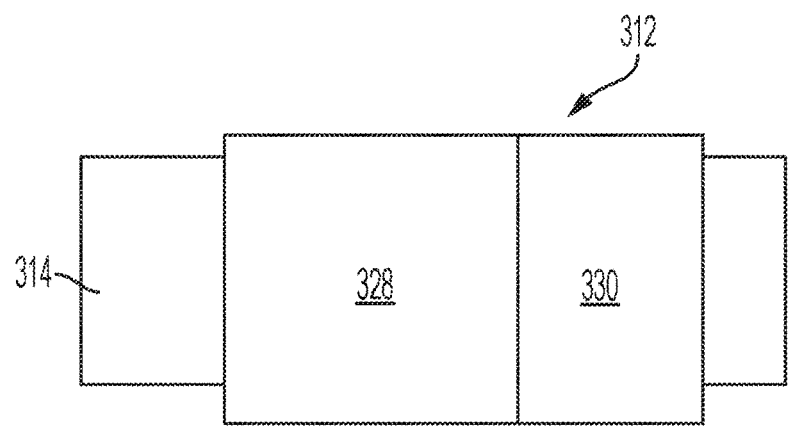
FIG. 3C illustrates a top view of the device illustrated in FIG. 3A.

FIGS. 3A-3C illustrate a front (3A), side (3B), and top (3C) view of an exemplary implantable closed-loop neuromodulation device with five curved members extending (302, 304, 306, 308, and 310) from a body 312, implanted on a nerve 314. The body of the device includes the integrated circuit 324, a non-transitory memory 326, a battery 328, and an ultrasonic transducer 330 (such as a piezoelectric transducer). As seen in FIG. 3A, the curved members can include a first portion 302a and a second portion 302b bridged by the body 312 at point 316. In some embodiments, the first portion 302a and the second portion 302b are directly connected, and the curved member is attached to the body through a connecting member. The curved members include a plurality of electrode pads 318 on the inner surface of the curved members, and the electrode pads 318 are radially positioned around an axis parallel to the length of the nerve. A separation 320 between the first portion 302a and the 302b is present along the curved member (which may be similarly present in other curved members of the device). The implantable device can be implanted by flexing the first portion and the second portion of the curved member outwardly, thereby expanding the size of the separation and allowing the nerve or other filamentous tissue to pass through the separation and fit within the cylindrical space formed by the curved members. The first portion and the second portion of the curved member can be released, which allows the curved member to wrap around the nerve or other filamentous tissue.

The plurality of electrode pads of the exemplary device shown in FIG. 3A are outside of the nerve, but in direct contact with the epineurium of the nerve. The nerve includes several fascicles 322 within the nerve. The electrode pads 318 within a curved member can be operated for targeted emission of an electrical pulse to one or more of the fascicles 322 or other subset of nerve fibers, and/or operated for targeted detection of an electrophysiological signal transmitted by one or more of the fascicles 322 or other subset of nerve fibers. For example, the electrode pads 318 can be selectively activated by the computational circuit within the integrated circuit 324, which is housed within the body 212, to emit an electric pulse targeted to one or more fascicles 322. In another example, the electrode pads 218 are operated by the computational circuit to detect an electrophysiological signal transmitted by one or more of the fascicles 322 within the nerve 314. The curved members can be configured to detect the electrophysiological signal transmitted by the nerve or a subset of nerve fibers, emit an electrical pulse to the nerve or targeted to a subset of nerve fibers, or both detect the electrophysiological signal transmitted by the nerve or a subset of nerve fibers and emit an electrical pulse to the nerve or targeted to a subset of nerve fibers. By way of example, curved members 302, 306, and 310 can be configured to detect the electrophysiological signal transmitted by the nerve or a subset of nerve fibers, and curved members 304 and 308 can be configured to emit an electrical pulse to the nerve or targeted to a subset of nerve fibers.

The one or more curved members of the implantable device are sized to engage a selected nerve or fibrous tissue containing a nerve. The nerve can be the spinal cord or a peripheral nerve. In some embodiments, the nerve is an autonomic nerve or a somatic nerve. In some embodiments, the nerve is a sympathetic nerve or a parasympathetic nerve. In some embodiments, the nerve is a vagus nerve, a mesenteric nerve, a splenic nerve, a sciatic nerve, a tibial nerve, a pudendal nerve, a celiac ganglion, a sacral nerve, or any branch thereof.

Targeted Detection of an Electrophysiological Signal

One or more of the curved members of the implantable device can be configured to detect the electrophysiological signal from a targeted subset of nerve fibers within the nerve. The subset of fibers can be, for example, one or more (e.g., 2, 3, 4, or more) fascicles, or a portion of one or more (e.g., 2, 3, 4, or more) fascicles within the nerve. In some embodiments, the subset of nerve fibers comprises or consists of afferent nerve fibers within the nerve, or a subset of afferent nerve fibers within the nerve. In some embodiments, the subset of nerve fibers comprises or consists of efferent nerve fibers within the nerve, or a subset of efferent nerve fibers within the nerve. In some embodiments, the subset of nerve fibers comprises or consists of efferent nerve fibers within two or more fascicles within the nerve or afferent nerve fibers within two or more fascicles within the nerve.

One or more techniques such as computational modeling (e.g., finite element models), inverse source estimation, multipole (e.g., tripole) neural recording, velocity-selective recording, or beamforming can be used to selectively target the subset of nerve fibers. See, for example, Taylor et al., *Multiple-electrode nerve cuffs for low-velocity and velocity selective neural recording*, Medical & Biological Engineering & Computing, vol. 42, pp. 634-643 (2004); and Wodlinger et al., *Localization and Recovery of Peripheral Neural Sources with Beamforming Algorithms*, IEEE Transactions on Neural Systems and Rehabilitation Engineering, vol. 17, no. 5, pp. 461468 (2009).

The computational circuit of the implantable device operates the plurality of electrodes on one or more curved members of the device for targeted detection of the electrophysiological signal. The computational circuit can analyze the electrophysiological signal detected by all or a subset of the electrode pads to determine the subset of nerve fibers within the nerve that are transmitting the electrophysiological signal. Certain nerves may transmit compound electrophysiological signal (or compound action potentials), which is the sum of the electrophysiological signals (or action potentials) simultaneously transmitted by two or more different subsets of nerve fibers. Based on the electrophysiological signal detected by the plurality of electrode pads, the computational circuit is able to determine which subset of nerve fibers transmits which electrophysiological signal. In some embodiments data received from the interrogator (such as temperature data, or data related to an analyte concentration or other physiological condition) is further used to determine which subset of nerve fibers transmits the electrophysiological signal.

For example, in some embodiments, the computational circuit is configured to selectively detect an electrophysiological signal from a targeted subset of nerve fibers using velocity-selective recording, which may be combined with multipolar (e.g., tripolar) recording (which can include any number of tripoles within the plurality of electrodes on one or more curved members).

Beamforming can additionally or alternatively be used to detect the electrophysiological signals from the targeted subset of nerve fibers. A portion of or all of the electrode pads of one or more curved members can detect the electrophysiological signal from the nerve, and the computational circuit can determine the cross-sectional location of the transmitted signal within the nerve based on the differences in electrophysiological signal detected by a portion or all of the electrode pads of the one or more curved members.

Stimulation of one or more nerves at a location separate from the location of the implanted device can result in a modulation of the electrophysiological signal at the location of the implanted device. The modulation of the electrophysiological signal detected at different subsets of nerve fibers within the nerve in electrical communication with the electrode pads of the device can be the result of stimulation in different distant nerves. For example, stimulation of the splenic nerve can result in modulation of an electrophysiological signal detected from first subset of nerve fibers within the vagus nerve, and stimulation of a renal nerve can result in modulation of an electrophysiological signal detected from a second subset of nerve fibers within the vagus nerve. Therefore, an implantable device positioned on the vagus nerve can detect an electrophysiological signal from the first subset of nerve fibers to monitor stimulation of the splenic nerve, and a second subset of nerve fibers to monitor stimulation of the renal nerve.

In some embodiments, the implantable device is positioned at a first nerve locus and is configured to detect stimulation of a second nerve locus by selectively detecting an electrophysiological signal from a subset of nerve fibers within the first nerve locus that is associated with the second nerve locus. In some embodiments, the first nerve locus and the second nerve locus are separated by one or more nerve branch points or one or more synapses. In some embodiments, the second nerve locus is proximal to the brain relative to the first nerve locus, and in some embodiment the second nerve locus is distal from the brain relative to the first nerve locus. In some embodiments, the targeted subset of nerve fibers comprises or consists of afferent nerve fibers. In some embodiments, the targeted subset of nerve fibers comprises or consists of efferent nerve fibers.

Targeted Stimulation of a Nerve

One or more of the curved members of the device can be configured to emit a targeted electrical pulse to a subset of nerve fibers within the nerve by selectively activating one or more electrode pads within the plurality of electrode pads on the curved member. The computational circuit of the device can operate the electrode pads to selectively activate the electrode pads. Selective activation can include, for example, activating a portion of the electrode pads within the plurality of electrode pads of one or more curved members and/or differentially activating all or a portion of the electrode pads within the plurality of electrode pads of the one or more curved members. The plurality of electrodes can therefore be operated to steer the electrical pulse emitted by the plurality of electrode pads to the target subset of nerve fibers. Techniques such as electrical field interference and/or multipolar stimulation (e.g., tripolar stimulation) can be used to target the electrical pulse to the subset of nerve fibers within the nerve. See, for example, Grossman, et al., *Noninvasive Deep Brain Stimulation via Temporally Interfering Electrical Fields*, Cell, vol. 169, pp. 1029-1041 (2017). The electrode pads with one or more curved members can be selectively activated by the computational circuit to target the emitted electrical pulse to the subset of nerve fibers.

The subset of nerve fibers targeted by the emitted electrical pulse can be the same or different as the subset of nerve fibers from which the electrophysiological signal is detected. The one or more curved member configured to emit the targeted electrical pulse can be the same or different as the one or more curved members on the device configured to detect the electrophysiological signal. The emitted targeted electrical pulse can stimulate the nerve at the position of the implantable device. The subset of nerve fibers targeted by the electrical pulse can be the same or a different subset of nerve fibers for which the electrophysiological signal is selectively detected.

The subset of nerve fibers targeted by the electrical pulse emitted by the device can be, for example, one or more (e.g., 2, 3, 4, or more) fascicles, or a portion of one or more (e.g., 2, 3, 4, or more) fascicles within the nerve. In some embodiments, the subset of nerve fibers comprises or consists of afferent nerve fibers within the nerve, or a subset of afferent nerve fibers within the nerve. In some embodiments, the subset of nerve fibers comprises or consists of efferent nerve fibers within the nerve, or a subset of efferent nerve fibers within the nerve. In some embodiments, the subset of nerve fibers comprises or consists of efferent nerve fibers within two or more fascicles within the nerve or afferent nerve fibers within two or more fascicles within the nerve.

Targeted stimulation of a subset of nerve fibers by emitting a targeted electrical pulse to the subset of nerve fibers can result in stimulation of a nerve at a location distant from the position of the nerve. The distant nerve stimulated by the implantable device depends on the subset of nerves at the position of the implantable device targeted by the electrical pulse emitted by the device. In some embodiments, the implantable device is positioned at a first nerve locus and is configured to stimulate a second nerve locus by emitting a targeted electrical pulse to a subset of nerve fibers within the first nerve locus that is associated with the second nerve locus. In some embodiments, the first nerve locus and the second nerve locus are separated by one or more nerve branch points or one or more synapses. In some embodiments, the second nerve locus is proximal to the brain relative to the first nerve locus, and in some embodiment the second nerve locus is distal from the brain relative to the first nerve locus. In some embodiments, the targeted subset of nerve fibers comprises or consists of afferent nerve fibers. In some embodiments, the targeted subset of nerve fibers comprises or consists of efferent nerve fibers.

Wireless Communication

Although the implantable device can emit an electrical pulse in response to a detected electrophysiological signal through a closed-loop, on-board computational circuit, in some embodiments there is a system that includes a closed-loop implantable device described herein and an interrogator configured to emit ultrasonic waves that power the device. The interrogator may be an external (i.e., non-implanted) device or a separate but fully implanted device. If implanted, the interrogator can wirelessly communicate with an external device, for example using ultrasonic communication or radiofrequency (RF). The ultrasonic transducer in the implantable device is configured to receive the ultrasonic waves emitted by the interrogator, which converts the energy from the ultrasonic waves into an electrical energy. The electrical energy can be stored in a battery in the device, if present, and can be used to power device components such as the computational circuit.

In some embodiments, the interrogator is configured to wirelessly communicate with the closed-loop implantable device through ultrasonic communication. The implantable device receives ultrasonic waves from the interrogator through the ultrasonic transducer of the implantable device. Optionally, the ultrasonic waves transmitted by the interrogator to the implantable device can encode instructions for operating the implantable device, which can be received by the computational circuit. Vibrations of the ultrasonic transducer on the implantable device caused by the ultrasonic waves generate a voltage across the electric terminals of the transducer, and current flows through the device, including the integrated circuit. The ultrasonic waves encoding the information or instructions emitted by the interrogator are received by the ultrasonic transducer in the implantable device. The information or instructions are then encoded in an electrical current flowing through the ultrasonic transducer resulting from receiving the ultrasonic waves, and the encoded information or instructions can be deciphered by the computational circuit. In some embodiments, the computational circuit stores the instructions or information on the non-transitory memory of the device.

Information encoded in the ultrasonic waves emitted by the interrogator and received by the closed-loop implantable device can include, for example, instructions for starting or stopping closed-loop neuromodulation, one or more calibration instructions, one or more updates to the operation software, and/or or one or more templates (such as template electrophysiological signals, one or more template electrophysiological signals, and/or one or more template stimulation signals). The information encoded in the ultrasonic waves can be processed by the computational circuit and/or stored on the non-transitory memory, if present. Calibration instructions for the device can include, for example, an association between (1) a subset of nerve fibers within the nerve, and (2) a nerve or a subset of nerve fibers, at a different nerve locus within the subject. In some embodiments, the association includes instructions for stimulating a second nerve locus by emitting targeted electrical pulse to a subset of nerve fibers within a first nerve locus in electrical communication with the device. In some embodiments, the association includes instructions for detecting stimulation of a second nerve locus by selectively detecting an electrophysiological signal from a subset of nerve fibers at a first nerve locus in electrical communication with the device.

Figure 4:
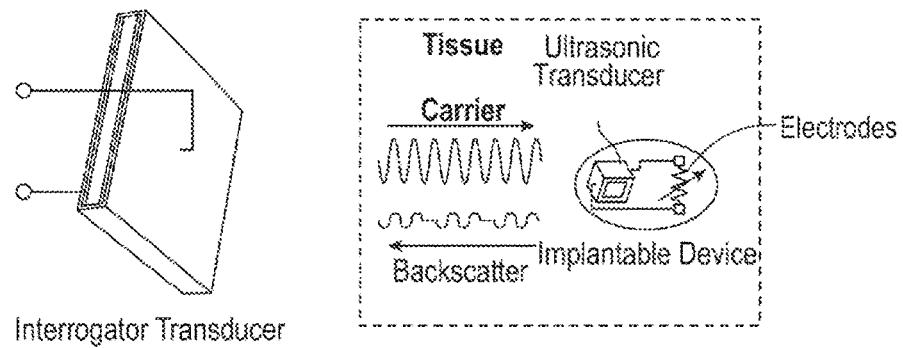
FIG. 4 shows an interrogator in communication with an implantable device through an ultrasonic transducer. The interrogator emits carrier waves, which are received by the implantable device. The implantable device then emits an ultrasonic backscatter, which can be received by the interrogator. Optionally, the ultrasonic backscatter encodes data or information about the implantable device.

In some embodiments, the closed-loop implantable device transmits information to the interrogator through ultrasonic backscatter. FIG. 4 shows an interrogator in communication with an implantable device through an ultrasonic transducer. The external ultrasonic transceiver emits ultrasonic waves ("carrier waves"), which can pass through tissue. The carrier waves cause mechanical vibrations on the ultrasonic transducer (e.g., a bulk piezoelectric transducer, a PUMT, or a CMUT). A voltage across the ultrasonic transducer is generated, which imparts a current flowing through an integrated circuit on the implantable device. The current flowing through to the ultrasonic transducer causes the transducer on the implantable device to emit backscatter ultrasonic waves. In some embodiments, the integrated circuit modulates the current flowing through the ultrasonic transducer to encode information, and the resulting ultrasonic backscatter waves encode the information. The backscatter waves can be detected by the interrogator, and can be analyzed to interpret information encoded in the ultrasonic backscatter.

Ultrasonic backscatter emitted from the implantable device can encode information relating to the implantable device. The ultrasonic backscatter can be received by the interrogator device (which may be the same or different from the interrogator that transmitted the ultrasonic waves received by the ultrasonic transducer in the implantable device), and deciphered to determine information encoded in the ultrasonic backscatter waves. The information can be encoded using a modulation circuit within the integrated circuit of the implantable device. The modulation circuit can modulate the current flowing through the ultrasonic transducer to encode the information. The modulated current flows through the ultrasonic transducer to modulate the ultrasonic backscatter, thereby encoding the information in the ultrasonic backscatter waves. The modulation circuit includes one or more switches, such as an on/off switch or a field-effect transistor (FET). An exemplary FET that can be used with some embodiments of the implantable device is a metal-oxide-semiconductor field-effect transistor (MOSFET). The modulation circuit can alter the impedance of a current flowing through the ultrasonic transducer, and variation in current flowing through the transducer encodes the information.

Information encoded in the ultrasonic backscatter emitted from the device can include information related to a detected electrophysiological signal, a detected physiological condition (e.g., temperature, pH, oxygen levels, pressure, etc.), information related to the device status (for example whether the device is in operation, or a stimulating capacitor status, such as stimulating capacitor charge), or information related to the emitted electrical pulse. For example, the information related to the detected electrophysiological signal can include information related to the subset of nerve fibers from which the electrophysiological signal is detected (e.g., location information), amplitude or frequency of the detected electrophysiological signal, similarity to a template electrophysiological pulse, and/or a time stamp of the detected electrophysiological signal. The information related to the detected physiological condition can include, for example, a temperature, a pH, an oxygen level, or a pressure; and/or a time stamp for the detected physiological condition. Information related to the emitted electrical pulse can include, for example, information related to the subset of nerve fibers (e.g., a targeted location of the emitted electrical pulse); an amplitude, frequency, or waveform of the emitted electrical pulse, and/or a time stamp of the emitted electrical pulse.

In some embodiments, information encoded in the ultrasonic backscatter includes a unique identifier for the implantable device, which is optionally a digitized unique identifier. This can be useful, for example, to ensure the interrogator is in communication with the correct implantable device when a plurality of implantable devices is implanted in the subject. In some embodiments, the information encoded in the ultrasonic backscatter includes a verification signal that verifies an electrical pulse was emitted by the implantable device. In some embodiments, the information encoded in the ultrasonic backscatter includes an amount of energy stored or a voltage in the energy storage circuit (or one or more capacitors in the energy storage circuit).

In some embodiments, the backscattered ultrasound is digitized by the implantable device. For example, the implantable device can include an oscilloscope or analog-to-digital converter (ADC) and/or a memory, which can digitally encode information in current (or impedance) fluctuations. The digitized current fluctuations, which can encode information, are received by the ultrasonic transducer, which then transmits digitized acoustic waves. The digitized data can compress the analog data, for example by using singular value decomposition (SVD) and least squares-based compression. In some embodiments, the compression is performed by a correlator or pattern detection algorithm. The backscatter signal may go through a series of non-linear transformation, such as $4^{th}$ order Butterworth bandpass filter rectification integration of backscatter regions to generate a reconstruction data point at a single time instance. Such transformations can be done either in hardware (i.e., hard-coded) or in software.

In some embodiments, the digitized signal compresses the size of the analog signal. The decreased size of the digitized signal can allow for more efficient reporting of information encoded in the ultrasonic backscatter. By compressing the size of the transmitted information through digitization, potentially overlapping signals can be accurately transmitted.

Communication between the interrogator and the implantable device can use a pulse-echo method of transmitting and receiving ultrasonic waves. In the pulse-echo method, the interrogator transmits a series of interrogation pulses at a predetermined frequency, and then receives backscatter echoes from the implanted device. In some embodiments, the pulses are square, rectangular, triangular, sawtooth, or sinusoidal. In some embodiments, the pulses output can be two-level (GND and POS), three-level (GND, NEG, POS), 5-level, or any other multiple-level (for example, if using 24-bit DAC). In some embodiments, the pulses are continuously transmitted by the interrogator during operation. In some embodiments, when the pulses are continuously transmitted by the interrogator a portion of the transducers on the interrogator are configured to receive ultrasonic waves and a portion of the transducers on the interrogator are configured to transmit ultrasonic waves. Transducers configured to receive ultrasonic waves and transducers configured to transmit ultrasonic waves can be on the same transducer array or on different transducer arrays of the interrogator. In some embodiments, a transducer on the interrogator can be configured to alternatively transmit or receive the ultrasonic waves. For example, a transducer can cycle between transmitting one or more pulses and a pause period. The transducer is configured to transmit the ultrasonic waves when transmitting the one or more pulses, and can then switch to a receiving mode during the pause period.

The interrogator includes one or more ultrasonic transducers, which can operate as an ultrasonic transmitter and/or an ultrasonic receiver (or as a transceiver, which can be configured to alternatively transmit or receive the ultrasonic waves). The one or more transducers can be arranged as a transducer array, and the interrogator can optionally include one or more transducer arrays. In some embodiments, the ultrasound transmitting function is separated from the ultrasound receiving function on separate devices. That is, optionally, the interrogator comprises a first device that transmits ultrasonic waves to the implantable device, and a second device that receives ultrasonic backscatter from the implantable device. In some embodiments, the transducers in the array can have regular spacing, irregular spacing, or be sparsely placed. In some embodiments the array is flexible. In some embodiments the array is planar, and in some embodiments the array is non-planar.

Figure 5:
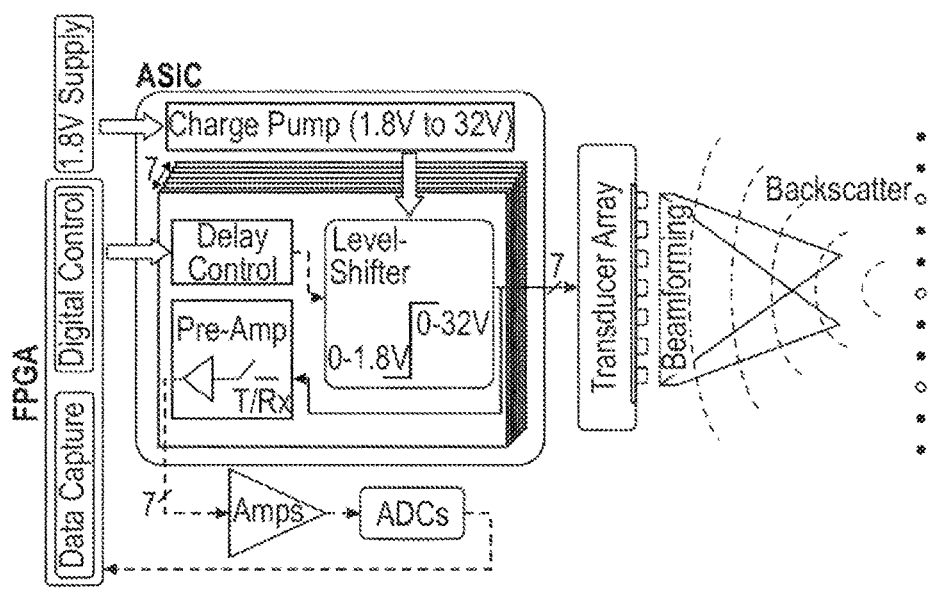
FIG. 5 illustrates an exemplary interrogator that can be used in a system including the implantable device described herein.

An exemplary interrogator is shown in FIG. 5. The illustrated interrogator shows a transducer array with a plurality of ultrasonic transducers. In some embodiments, the transducer array includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more transducers. In some embodiments, the transducer array includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer transducers. The transducer array can be, for example a chip comprising 50 or more ultrasonic transducer pixels.

The interrogator shown in FIG. 5 illustrates a single transducer array; however the interrogator can include 1 or more, 2 or more, or 3 or more separate arrays. In some embodiments, the interrogator includes 10 or fewer transducer arrays (such as 9, 8, 7, 6, 5, 4, 3, 2, or 1 transducer arrays). The separate arrays, for example, can be placed at different points of a subject, and can communicate to the same or different implantable devices. In some embodiments, the arrays are located on opposite sides of an implantable device. The interrogator can include an application specific integrated circuit (ASIC), which includes a channel for each transducer in the transducer array. In some embodiments, the channel includes a switch (indicated in FIG. 5 by "T/Rx"). The switch can alternatively configure the transducer connected to the channel to transmit ultrasonic waves or receive ultrasonic waves. The switch can isolate the ultrasound receiving circuit from the higher voltage ultrasound transmitting circuit.

In some embodiments, the transducer connected to the channel is configured only to receive or only to transmit ultrasonic waves, and the switch is optionally omitted from the channel. The channel can include a delay control, which operates to control the transmitted ultrasonic waves. The delay control can control, for example, the phase shift, time delay, pulse frequency and/or wave shape (including amplitude and wavelength). The delay control can be connected to a level shifter, which shifts input pulses from the delay control to a higher voltage used by the transducer to transmit the ultrasonic waves. In some embodiments, the data representing the wave shape and frequency for each channel can be stored in a 'wave table'. This allows the transmit waveform on each channel to be different. Then, delay control and level shifters can be used to stream data to the actual transmit signals to the transducer array. In some embodiments, the transmit waveform for each channel can be produced directly by a high-speed serial output of a microcontroller or other digital system and sent to the transducer element through a level shifter or high-voltage amplifier. In some embodiments, the ASIC includes a charge pump (illustrated in FIG. 5) to convert a first voltage supplied to the ASIC to a higher second voltage, which is applied to the channel. The channels can be controlled by a controller, such as a digital controller, which operates the delay control.

In the ultrasound receiving circuit, the received ultrasonic waves are converted to current by the transducers (set in a receiving mode), which is transmitted to a data capture circuit. In some embodiments, an amplifier, an analog-to-digital converter (ADC), a variable-gain-amplifier, or a time-gain-controlled variable-gain-amplifier which compensates for tissue loss, and/or a band pass filter is included in the receiving circuit. The ASIC can draw power from a power supply, such as a battery (which is preferred for a wearable embodiment of the interrogator). In the embodiment illustrated in FIG. 5, a 1.8V supply is provided to the ASIC, which is increased by the charge pump to 32V, although any suitable voltage can be used. In some embodiments, the interrogator includes a processor and or a non-transitory computer readable memory. In some embodiments, the channel described above does not include a T/Rx switch but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, the transducer array contains more transducer elements than processing channels in the interrogator transmit/receive circuitry, with a multiplexer choosing different sets of transmitting elements for each pulse. For example, 64 transmit receive channels connected via a 3:1 multiplexer to 192 physical transducer elements—with only 64 transducer elements active on a given pulse.

By way of example, in some embodiments the interrogator, or the transducer(s) of the interrogator, is wearable. For example, the interrogator, or the transducer(s) of the interrogator, may be fixed to the body by a strap or adhesive. In another example, the interrogator can be a wand, which may be held by a user (such as a healthcare professional). In some embodiments, the interrogator can be held to the body via suture, simple surface tension, a clothing-based fixation device such as a cloth wrap, a sleeve, an elastic band, or by sub-cutaneous fixation. The transducer or transducer array of the interrogator may be positioned separately from the rest of the transducer. For example, the transducer array can be fixed to the skin of a subject at a first location (such as proximal to one or more implanted devices), and the rest of the interrogator may be located at a second location, with a wire tethering the transducer or transducer array to the rest of the interrogator.

The specific design of the transducer array of the interrogator depends on the desired penetration depth, aperture size, and size of the individual transducers within the array. The Rayleigh distance, R, of the transducer array is computed as:

$$R = \frac{D^2 - \lambda^2}{4\lambda} \approx \frac{D^2}{4\lambda}, D^2 \gg \lambda^2$$

where D is the size of the aperture and X is the wavelength of ultrasound in the propagation medium (i.e., the tissue). As understood in the art, the Rayleigh distance is the distance at which the beam radiated by the array is fully formed. That is, the pressure filed converges to a natural focus at the Rayleigh distance in order to maximize the received power. Therefore, in some embodiments, the implantable device is approximately the same distance from the transducer array as the Rayleigh distance.

The individual transducers in a transducer array can be modulated to control the Raleigh distance and the position of the beam of ultrasonic waves emitted by the transducer array through a process of beamforming or beam steering. Techniques such as linearly constrained minimum variance (LCMV) beamforming can be used to communicate a plurality of implantable devices with an external ultrasonic transceiver. See, for example, Bertrand et al., Beamforming Approaches for Untethered, Ultrasonic Neural Dust Motes for Cortical Recording: a Simulation Study, IEEE EMBC (August 2014). In some embodiments, beam steering is performed by adjusting the power or phase of the ultrasonic waves emitted by the transducers in an array.

In some embodiments, the interrogator includes one or more of instructions for beam steering ultrasonic waves using one or more transducers, instructions for determining the relative location of one or more implantable devices, instructions for monitoring the relative movement of one or more implantable devices, instructions for recording the relative movement of one or more implantable devices, and instructions for deconvoluting backscatter from a plurality of implantable devices.

Optionally, the interrogator is controlled using a separate computer system, such as a mobile device (e.g., a smartphone or a table). The computer system can wirelessly communicate to the interrogator, for example through a network connection, a radiofrequency (RF) connection, or Bluetooth. The computer system may, for example, turn on or off the interrogator or analyze information encoded in ultrasonic waves received by the interrogator.

In some embodiments, an interrogator communicates with a plurality of implantable devices. This can be performed, for example, using multiple-input, multiple output (MIMO) system theory. For example, communication between the interrogator and the plurality of implantable devices using time division multiplexing, spatial multiplexing, or frequency multiplexing. The interrogator can receive a combined backscatter from the plurality of the implantable devices, which can be deconvoluted, thereby extracting information from each implantable device. In some embodiments, interrogator focuses the ultrasonic waves transmitted from a transducer array to a particular implantable device through beam steering. The interrogator focuses the transmitted ultrasonic waves to a first implantable device, receives backscatter from the first implantable device, focuses transmitted ultrasonic waves to a second implantable device, and receives backscatter from the second implantable device. In some embodiments, the interrogator transmits ultrasonic waves to a plurality of implantable devices, and then receives ultrasonic waves from the plurality of implantable devices.

Exemplary Embodiments

The foregoing description has been described with reference to specific embodiments. Additional exemplary embodiments are provided below. However, the illustrative discussions and exemplary embodiments above are not intended to be exhaustive or to limit the disclosure to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure has been fully described with reference to the accompanying figures, it is to be noted that various changes and modifications will become apparent to those skilled in the art. Such changes and modifications are to be understood as being included within the scope of the disclosure and examples as defined by the claims.

The following embodiments are exemplary and are not intended to limit the claimed invention.

Embodiment 1. An implantable closed-loop neuromodulation device, comprising:
  one or more curved members extending from a body, the curved members comprising one or more electrode pads configured to at least partially surround an axis parallel to the length of a nerve, or a plurality of electrode pads configured to be radially positioned around the axis parallel to the length of the nerve;
  the body comprising:
    an ultrasonic transducer configured to receive ultrasonic waves and convert energy from the ultrasonic waves into an electrical energy; and
    a computational circuit electrically connected to the one or more electrode pads or the plurality of electrode pads, configured to:
      receive a detection signal based on a detected electrophysiological signal,
      generate a stimulation signal based on the detection signal, and
      operate the one or more electrode pads or the plurality of electrode pads of at least one of the one or more curved members to emit an electrical pulse to the nerve based on the stimulation signal.

Embodiment 2. The device of embodiment 1, wherein the curved members comprise the one or more electrode pads configured to at least partially surround the axis parallel to the length of the nerve.

Embodiment 3. The device of embodiment 2, wherein the one or more electrode pads surrounds the axis parallel to the length of the nerve by at least 50%.

Embodiment 4. The device of embodiment 2, wherein the one or more electrode pads surrounds the axis parallel to the length of the nerve by at least 100%.

Embodiment 5. The device of any one of embodiments 1-4, wherein the one or more electrode pads configured to at least partially surround the axis parallel to the length of a nerve comprise two or more electrode pads on the same curved member.

Embodiment 6. The device of any one embodiments 1-5, wherein the electrode pads configured to at least partially surround the axis parallel to the length of the nerve partially surround the axis parallel to the length of the nerve in a cross-sectional plane of the nerve.

Embodiment 7. The device of any one of embodiments 1-6, wherein the curved members comprise the plurality of electrode pads configured to be radially positioned around the axis parallel to the length of the nerve.

Embodiment 8. An implantable closed-loop neuromodulation device, comprising:
  one or more curved members extending from a body, each curved member comprising a plurality of electrode pads configured to be radially positioned around an axis parallel to the length of a nerve;
  the body comprising:
    an ultrasonic transducer configured to receive ultrasonic waves and convert energy from the ultrasonic waves into an electrical energy; and
    a computational circuit electrically connected to the plurality of electrode pads, configured to:
      receive a detection signal based on a detected electrophysiological signal,
      generate a stimulation signal based on the detection signal, and
      operate the plurality of electrode pads of at least one of the one or more curved members to emit an electrical pulse to the nerve based on the stimulation signal.

Embodiment 9. The device of any one of embodiments 1-8, wherein the plurality of electrode pads comprises three or more electrode pads.

Embodiment 10. The device of any one of embodiments 1-9, wherein the electrode pads within the plurality of electrode pads are radially positioned in a common plane of the nerve.

Embodiment 11. The device of any one of embodiments 1-10, wherein the device is configured to detect the electrophysiological signal from a targeted subset of nerve fibers within the nerve.

Embodiment 12. The device of embodiment 11, wherein the device is configured to detect the electrophysiological signal from one or more targeted fascicles within the nerve, one or more targeted afferent nerve fibers within the nerve, or one or more targeted efferent nerve fibers within the nerve.

Embodiment 13. The device of embodiment 11, wherein the device is configured to detect the electrophysiological signal from two or more different targeted fascicles within the nerve.

Embodiment 14. The device of any one of embodiments 1-13, wherein the device is configured to emit the electrical pulse to a targeted subset of nerve fibers within the nerve.

Embodiment 15. The device of embodiment 14, wherein the device is configured to emit the electrical pulse to one or more targeted fascicles within the nerve, one or more targeted afferent nerve fibers within the nerve, or one or more targeted efferent nerve fibers within the nerve.

Embodiment 16. The device of embodiment 14, wherein the device is configured to emit the electrical pulse to two or more different targeted fascicles within the nerve.

Embodiment 17. The device of any one of embodiments 1-16, wherein the device is configured to detect the electrophysiological signal from a first targeted subset of nerve fibers within the nerve, and to emit the electrical pulse to a second targeted subset of nerve fibers within the nerve, wherein the first targeted subset of nerve fibers and the second targeted subset of nerve fibers are the same or different.

Embodiment 18. The device of any one of embodiments 1-17, wherein the body further comprises a battery configured to receive the electrical energy from the ultrasonic transducer and power the computational circuit.

Embodiment 19. The device of any one of embodiments 1-18, wherein the device comprises a non-transitory memory.

Embodiment 20. The device of embodiment 19, wherein the non-transitory memory is configured to store data comprising data based on the detected electrophysiological signal, data based on the emitted electrical pulse, or data based on a detected or measured physiological condition.

Embodiment 21. The device of embodiment 19 or 20, wherein the non-transitory memory is configured to store data received from an interrogator.

Embodiment 22. The device of embodiment 20 or 21, wherein the ultrasonic transducer is configured to emit ultrasonic backscatter waves that encode at least a portion of the data.

Embodiment 23. The device of any one of embodiments 20-22, wherein the data comprises a time stamp, a velocity, a direction, an amplitude, a frequency, or a waveform of the detected electrophysiological signal or the emitted electrical pulse.

Embodiment 24. The device of any one of embodiments 19-23, wherein the non-transitory memory is configured to store data acquired over a period of time.

Embodiment 25. The device of any one of embodiments 19-24, wherein the non-transitory memory stores one or more template detection signals or one or more template pulses.

Embodiment 26. The device of embodiment 25, wherein the computational circuit is configured to generate the stimulation signal by comparing the detection signal to the one or more template detection signals.

Embodiment 27. The device of embodiment 25 or 26, wherein generating the stimulation signal comprises retrieving a template pulse from the non-transitory memory, and generating the stimulation signal based on the retrieved template pulse.

Embodiment 28. The device of any one of embodiments 1-24, wherein the stimulation signal is generated using a mathematical relationship between the detection single and the stimulation signal.

Embodiment 29. The device of any one of embodiments 1-28, wherein the device further comprises a sensor configured to detect or measure a physiological condition.

Embodiment 30. The device of embodiment 29, wherein the physiological condition is temperature, pH, pressure, heart rate, strain, or presence or amount of an analyte.

Embodiment 31. The device of embodiment 29 or 30, wherein the detection signal comprises a detected electrophysiological pulse component and an additional detected physiological condition component.

Embodiment 32. The device of any one of embodiments 1-31, wherein the device comprises a first curved member comprising a first plurality of electrode pads and a second curved member comprising a second plurality of electrode pads, wherein the first plurality of electrode pads and the second plurality of electrode pads are each configured to be radially positioned around the axis parallel to the length of the nerve at different positions along the length of the nerve.

Embodiment 33. The device of embodiment 32, wherein the first plurality of electrode pads and the second plurality of electrode pads are configured to detect the electrophysiological signal transmitted by the nerve.

Embodiment 34. The device of embodiment 32 or 33, wherein the device further comprises a third curved member comprising a third plurality of electrode pads, wherein the third plurality of electrode pads is configured to be radially positioned around the axis parallel to the length of the nerve at a position between the first curved member and the second curved member along the length of the nerve.

Embodiment 35. The device of any one of embodiments 32-34, wherein the computational circuit is configured to determine a subset of nerve fibers that transmits the electrophysiological signal based on the electrophysiological signal detected by one or more of the first plurality of electrode pads, the second plurality of electrode pads, or the third plurality of electrode pads.

Embodiment 36. The device of embodiment 35, wherein the subset of nerve fibers that transmits the electrophysiological signal is further determined based on data received from an interrogator.

Embodiment 37. The device of any one of embodiments 32-36, wherein the first plurality of electrode pads, the second plurality of electrode pads, or the third plurality of electrode pads is configured to emit the electrical pulse to the nerve.

Embodiment 38. The device of embodiment 37, wherein the electrode pads within the first plurality of electrode pads, the second plurality of electrode pads, or the third plurality of electrode pads is configured to be selectively activated to emit the electrical pulse to a targeted subset of nerve fibers within the nerve.

Embodiment 39. The device of any one of embodiments 1-38, wherein the device comprises:
- a first curved member comprising a first plurality of electrode pads, and a second curved member comprising a second plurality of electrode pads, the first plurality of electrode pads and the second plurality of electrode pads configured to detect the electrophysiological signal transmitted by the nerve; and
- a third curved member comprising a third plurality of electrode pads, and a fourth curved member comprising a fourth plurality of electrode pads, the third plurality of electrode pads and the fourth plurality of electrode pads configured to emit the electrical pulse;
- wherein the first plurality of electrode pads, the second plurality of electrode pads, the third plurality of electrode pads, and the fourth plurality of electrode pads are each configured to be radially positioned around the axis parallel to the nerve at different positions along the length of the nerve.

Embodiment 40. The device of embodiment 39, wherein the third curved member and the fourth curved member are positioned between the first curved member and the second curved member along the length of the nerve.

Embodiment 41. The device of embodiment 39 or 40, further comprising a fifth curved member comprising a fifth plurality of electrode pads configured to detect the electrophysiological signal.

Embodiment 42. The device of embodiment 41, wherein the fifth curved member is positioned between the third curved member and the fourth curved member along the length of the nerve.

Embodiment 43. The device of embodiment 41 or 42, wherein the computational circuit is configured to determine a subset of nerve fibers that transmits the electrophysiological signal based on the electrophysiological signal detected by one or more of the first plurality of electrode pads, the second plurality of electrode pads, or the fifth plurality of electrode pads.

Embodiment 44. The device of embodiment 43, wherein the subset of nerve fibers that transmits the electrophysiological signal is further determined based on data received from an interrogator.

Embodiment 45. The device of any one of embodiments 39-44, wherein the electrode pads within the third plurality of electrode pads or the fourth plurality of electrode pads is configured to be selectively activated to emit the electrical pulse to a targeted subset of nerve fibers within the nerve.

Embodiment 46. The device of any one of embodiments 1-31, wherein the device comprises a first curved member comprising a first electrode pad and a second curved member, wherein the first of electrode pad and the second electrode pad are each configured to at least partially surround the axis parallel to the length of the nerve at different positions along the length of the nerve.

Embodiment 47. The device of embodiment 46, wherein the first electrode pad and the second electrode pad are configured to detect the electrophysiological signal transmitted by the nerve.

Embodiment 48. The device of embodiment 46 or 47, wherein the device further comprises a third curved member comprising a third electrode pad configured to at least partially surround the axis parallel to the length of the nerve at a position between the first curved member and the second curved member along the length of the nerve.

Embodiment 49. The device of any one of embodiments 4648, wherein the computational circuit is configured to determine a subset of nerve fibers that transmits the electrophysiological signal based on the electrophysiological signal detected by one or more of the first electrode pad, the second electrode pad, or the third electrode pad.

Embodiment 50. The device of embodiment 49, wherein the subset of nerve fibers that transmits the electrophysiological signal is further determined based on data received from an interrogator.

Embodiment 51. The device of any one of embodiments 46-50, wherein the first electrode pad, the second electrode pad, or the third electrode pad is configured to emit the electrical pulse to the nerve.

Embodiment 52. The device of embodiment 51, wherein the first electrode pad, the second electrode pad, or the third electrode pad is configured to be selectively activated to emit the electrical pulse to a targeted subset of nerve fibers within the nerve.

Embodiment 53. The device of any one of embodiments 1-31, wherein the device comprises:

a first curved member comprising a first of electrode pad and a second curved member comprising a second electrode pad, the first electrode pad and the second electrode pad configured to detect the electrophysiological signal transmitted by the nerve; and a third curved member comprising a third electrode pad, and a fourth curved member comprising a fourth electrode pad, the third electrode pas and the fourth electrode pad configured to emit the electrical pulse;

wherein the first electrode pad, the second electrode pad, the third electrode pad, and the fourth electrode pad are configured to at least partially surround an axis parallel to the length of a nerve at different positions along the length of the nerve.

Embodiment 54. The device of embodiment 53, wherein the third curved member and the fourth curved member are positioned between the first curved member and the second curved member along the length of the nerve.

Embodiment 55. The device of embodiment 53 or 54, further comprising a fifth curved member comprising a fifth electrode pad configured to detect the electrophysiological signal.

Embodiment 56. The device of embodiment 55, wherein the fifth curved member is positioned between the third curved member and the fourth curved member along the length of the nerve.

Embodiment 57. The device of embodiment 55 or 56, wherein the computational circuit is configured to determine a subset of nerve fibers that transmits the electrophysiological signal based on the electrophysiological signal detected by one or more of the first electrode pad, the second electrode pad, or the fifth electrode pad.

Embodiment 58. The device of embodiment 57, wherein the subset of nerve fibers that transmits the electrophysiological signal is further determined based on data received from an interrogator.

Embodiment 59. The device of any one of embodiments 53-58, wherein the third electrode pads or the fourth electrode pad is configured to be selectively activated to emit the electrical pulse to a targeted subset of nerve fibers within the nerve.

Embodiment 60. The device of any one of embodiments 1-59, wherein the computational circuit is configured to determine a direction or a velocity of the electrophysiological signal.

Embodiment 61. The device of any one of embodiments 1-60, wherein the one or more electrode pads or the plurality of electrode pads is configured to be positioned outside of the nerve and in electrical communication with the nerve.

Embodiment 62. The device of embodiment 61, wherein the one or more electrode pads or the plurality of electrode pads is configured to be in contact with the epineurium of the nerve.

Embodiment 63. The device of any one of embodiments 1-62, wherein the one or more electrode pads or the plurality of electrode pads is configured to penetrate the epineurium of the nerve at one or more locations.

Embodiment 64. The device of any one of embodiments 1-63, wherein the computational circuit is configured to downsample the detection signal or a component of the detection signal.

Embodiment 65. The device of any one of embodiments 1-64, wherein the computational circuit is configured to generate the stimulation signal based on a direction, a velocity, a frequency, an amplitude, or a waveform of a compound action potential or a subset of the compound action potential transmitted by the nerve or a subset of nerve fibers within the nerve.

Embodiment 66. The device of any one of embodiments 1-65, wherein the stimulation signal comprises a timing, amplitude, frequency, or waveform of the electrical pulse emitted by the device.

Embodiment 67. A system, comprising the device of any one of embodiments 1-66 and an interrogator configured to emit ultrasonic waves that power the device.

Embodiment 68. The system of embodiment 67, wherein the interrogator is an external device.

Embodiment 69. The system of embodiment 67 or 68, wherein:
the device comprises a non-transitory memory configured to store data based on the detected electrophysiological signal or the emitted electrical pulse,
the ultrasonic transducer is configured to emit ultrasonic backscatter waves that encode at least a portion of the data, and
the interrogator is configured to receive the ultrasonic backscatter waves.

Embodiment 70. The system of embodiment 69, wherein the interrogator is further configured to decode the data.

Embodiment 71. A method of modulating neural activity, comprising:
receiving ultrasonic waves at an ultrasonic transducer on a fully implanted closed-loop neuromodulation device;
converting the ultrasonic waves into an electrical energy that powers the device;
detecting, using the device, an electrophysiological signal transmitted by a targeted subset of nerve fibers within a nerve;
generating, using the device, a stimulation signal based on the detected electrophysiological signal;
emitting, using the device, an electrical pulse to the nerve based on the generated stimulation signal.

Embodiment 72. The method of embodiment 71, wherein the electrical pulse is emitted to a second targeted subset of nerve fibers within the nerve.

Embodiment 73. A method of modulating neural activity, comprising:
receiving ultrasonic waves at an ultrasonic transducer on a fully implanted closed-loop neuromodulation device;
converting the ultrasonic waves into an electrical energy that powers the device;
detecting, using the device, an electrophysiological signal transmitted by a nerve;
generating, using the device, a stimulation signal based on the detected electrophysiological signal;
emitting, using the device, an electrical pulse to a targeted subset of nerve fibers within the nerve based on the generated stimulation signal.

Embodiment 74. The method of any one of embodiments 71-73, comprising storing the electrical energy on a battery within the device.

Embodiment 75. The method of any one of embodiments 71-74, comprising storing data based on the detected electrophysiological signal or the emitted electrical pulse on a non-transitory memory within the device.

Embodiment 76. The method of embodiment 75, wherein the data comprise a time stamp, a frequency, an amplitude, a waveform, a velocity, or a direction of the detected electrophysiological signal or the emitted electrical pulse.

Embodiment 77. The method of any one of embodiments 71-76, comprising receiving data from an interrogator.

Embodiment 78. The method of embodiment 77, wherein the data is encoded in ultrasonic waves transmitted by the interrogator.

Embodiment 79. The method of embodiment 77 or 78, wherein the data received from the interrogator is stored on a non-transitory memory within the device.

Embodiment 80. The method of any one of embodiments 71-79, comprising emitting an ultrasonic backscatter encoding at least a portion of the data stored on the non-transitory medium.

Embodiment 81. The method of any one of embodiments 71-79, comprising determining a direction or a velocity of the detected electrophysiological signal.

Embodiment 82. The method of any one of embodiments 71-81, comprising detecting or measuring a physiological condition.

Embodiment 83. The method of embodiment 82, wherein the physiological condition comprises temperature, pH, pressure, heart rate, strain, and/or presence or amount of an analyte.

Embodiment 84. The method of any one of embodiments 71-83, comprising downsampling the detected electrophysiological signal prior to generating the stimulation signal.

Embodiment 85. The method of any one of embodiments 71-84, wherein the stimulation signal is generated based on a frequency, amplitude, or waveform of the detected electrophysiological signal.

What is claimed is:

1. A method of modulating neural activity, comprising:
receiving ultrasonic waves at an ultrasonic transducer on a fully implanted closed-loop neuromodulation device;
converting the ultrasonic waves into an electrical energy that powers the device;
detecting, using the device, an electrophysiological signal transmitted by a selectively targeted subset of nerve fibers within a nerve, wherein the selectively targeted subset of nerve fibers consists of less than all nerve fibers within the nerve;
generating, using the device, a stimulation signal based on the detected electrophysiological signal;
emitting, using the device, an electrical pulse to the nerve based on the generated stimulation signal.

2. The method of claim 1, wherein the neuromodulation device comprises a plurality of electrode pads, and the detecting comprises selectively operating one or more electrodes in the plurality of electrodes.

3. The method of claim 1, wherein the selectively targeted subset of nerve fibers consists of a selectively targeted subset of fascicles within the nerve.

4. The method of claim 3, wherein the selectively targeted subset of fascicles consists of 1 to 4 fascicles within the nerve.

5. The method of claim 1, wherein the selectively targeted subset of nerve fibers consists of afferent nerve fibers or consists of efferent nerve fibers.

6. The method of claim 1, wherein the electrical pulse is emitted to a second selectively targeted subset of nerve fibers within the nerve.

7. The method of claim 1, comprising storing the electrical energy on a battery within the device.

8. The method of claim 1, comprising storing data based on the detected electrophysiological signal on a non-transitory memory within the device.

9. The method of claim 8, wherein the data comprise a time stamp, a frequency, an amplitude, a waveform, a velocity, or a direction of the detected electrophysiological signal.

10. The method of claim 8, comprising receiving the data at an interrogator.

11. The method of claim 8, wherein the data is encoded in ultrasonic waves received by the interrogator.

12. The method of claim 1, comprising determining a direction or a velocity of the detected electrophysiological signal.

13. The method of claim 1, comprising detecting or measuring a physiological condition.

14. The method of claim 13, wherein the physiological condition comprises temperature, pH, pressure, heart rate, strain, or presence or amount of an analyte.

15. The method of claim 1, comprising downsampling the detected electrophysiological signal prior to generating the stimulation signal.

16. The method of claim 1, wherein the stimulation signal is generated based on a frequency, amplitude, or waveform of the detected electrophysiological signal.

17. A method of modulating neural activity, comprising:
receiving ultrasonic waves at an ultrasonic transducer on a fully implanted closed-loop neuromodulation device;
converting the ultrasonic waves into an electrical energy that powers the device;
detecting, using the device, an electrophysiological signal transmitted by a nerve;
generating, using the device, a stimulation signal based on the detected electrophysiological signal;
emitting, using the device, an electrical pulse to a selectively targeted subset of nerve fibers within the nerve based on the generated stimulation signal, wherein the selectively targeted subset of nerve fibers consists of less than all nerve fibers within the nerve.

18. The method of claim 17, wherein the neuromodulation device comprises a plurality of electrode pads, and the emitting comprises selectively activating one or more electrodes in the plurality of electrodes.

19. The method of claim 17, wherein the selectively targeted subset of nerve fibers consists of a selectively targeted subset of fascicles within the nerve.

20. The method of 19, wherein the selectively targeted subset of fascicles consists of 1 to 4 fascicles within the nerve.

21. The method of claim 17, wherein the selectively targeted subset of nerve fibers consists of afferent nerve fibers or consists of efferent nerve fibers.

22. The method of claim 17, comprising storing the electrical energy on a battery within the device.

23. The method of claim 17, comprising storing data based on the emitted electrical pulse on a non-transitory memory within the device.

24. The method of claim 23, wherein the data comprise a time stamp, a frequency, an amplitude, a waveform, a velocity, or a direction of the emitted electrical pulse.

25. The method of claim 17, comprising receiving data from an interrogator.

26. The method of claim 25, wherein the data is encoded in ultrasonic waves transmitted by the interrogator.

27. The method of claim 25, wherein the data received from the interrogator is stored on a non-transitory memory within the device.

28. The method of claim 23, comprising emitting an ultrasonic backscatter encoding at least a portion of the data stored on the non-transitory medium.

29. The method of claim 17, comprising determining a direction or a velocity of the detected electrophysiological signal.

30. The method of claim 17, comprising detecting or measuring a physiological condition.

31. The method of claim 30, wherein the physiological condition comprises temperature, pH, pressure, heart rate, strain, and/or presence or amount of an analyte.

32. The method of claim 17, comprising downsampling the detected electrophysiological signal prior to generating the stimulation signal.

33. The method of claim 17, wherein the stimulation signal is generated based on a frequency, amplitude, or waveform of the detected electrophysiological signal.

\* \* \* \* \*